United States Patent [19]
Ema et al.

[11] Patent Number: 5,779,634
[45] Date of Patent: Jul. 14, 1998

[54] MEDICAL INFORMATION PROCESSING SYSTEM FOR SUPPORTING DIAGNOSIS

[75] Inventors: Takehiro Ema; Eitaro Nishihara, both of Otawara, Japan

[73] Assignee: Kabushiki Kaisha Toshiba, Kawasaki, Japan

[21] Appl. No.: 315,496

[22] Filed: Sep. 30, 1994

Related U.S. Application Data

[63] Continuation of Ser. No. 880,522, May 8, 1992, abandoned.

[30] Foreign Application Priority Data

| May 10, 1991 | [JP] | Japan | 3-105851 |
| May 10, 1991 | [JP] | Japan | 3-105852 |
| Sep. 3, 1991 | [JP] | Japan | 3-222999 |

[51] Int. Cl.$^6$ ............................................. A61B 5/05
[52] U.S. Cl. ............................................. 600/407; 128/920
[58] Field of Search ................. 128/653.1, 920, 128/922; 364/413.02, 413.03, 413.13, 413.22

[56] References Cited

U.S. PATENT DOCUMENTS

| 3,970,996 | 7/1976 | Yasaka et al. | 364/413.02 |
| 4,616,319 | 10/1986 | Peters et al. | 364/413.13 |
| 4,653,112 | 3/1987 | Ouimette | 386/69 |
| 4,737,912 | 4/1988 | Ichikawa | 364/413.02 |
| 4,833,625 | 5/1989 | Fisher et al. | 395/139 |
| 4,851,984 | 7/1989 | Doi et al. | 364/413.23 |
| 4,887,211 | 12/1989 | Thiel et al. | 364/413.13 |
| 4,907,156 | 3/1990 | Doi et al. | 364/413.13 |
| 5,019,976 | 5/1991 | Chiu et al. | 364/413.13 |
| 5,133,020 | 7/1992 | Giger et al. | 382/6 |
| 5,140,518 | 8/1992 | Ema | 364/413.13 |
| 5,272,625 | 12/1993 | Nishihara et al. | 364/413.13 |

FOREIGN PATENT DOCUMENTS

| 140466 | 7/1985 | Japan | G06F 15/42 |
| 2165069 | 4/1986 | Japan | G06F 15/40 |

OTHER PUBLICATIONS

Fujimoto: "Picture Managing System in Hospital"; 61–154086; Jan. 1988; Abstracts of Japan; vol. 12 No. 214.
Ema; "Picture Information Keeping Communication Equipment"; 63–256726; Abstracts of Japan; vol. 14 No. 317.
Ema; "Picture Display Control Device"; 63–272439; May 1990; Abstracts of Japan; vol. 14 No. 330.

*Primary Examiner*—Brian L. Casler
*Attorney, Agent, or Firm*—Oblon, Spivak, McClelland, Maier & Neustadt, P.C.

[57] ABSTRACT

A medical information processing system for supporting diagnostic interpretation, featuring a data storage unit for storing an interpretation image and interpretation reference images for which a doctor will refer to interpret the interpretation image. A data loading unit loads the interpretation reference images from the data storage unit into a workstation unit according to a predetermined priority order. The data loading unit loads the images into a workstation which is selected from the workstation unit according to workstation vs. interpretation examination modality information. A diagnostic information creation unit creates diagnostic information relative to the image by inputting the doctor's findings or computerizing with a computer unit. Positions of abnormalities and degrees of the abnormalities are determined, and positions in association with the images are calculated. A diagnostic information comparing unit compares the diagnostic information with each other and creates differences between the diagnostic information as time-sequential abnormality change data. A diagnostic information output unit outputs the diagnostic information or results of comparing the diagnostic information with each other and superimposes the contents of the time-sequential abnormality change data on the associated image. The diagnostic information output unit also outputs predetermined contents for an inconsistency of the diagnostic information for the doctor's findings with the diagnostic information for the results of computerizing and includes a plurality of displays and automatically determines relational positions in which the images are displayed on the displays according to a predetermined relational information.

55 Claims, 22 Drawing Sheets

58

| PATIENT | PATIENT NAME : |
| | PATIENT ID NUMBER : |
| | DATE OF BIRTH : |
| | SEX : |
| EXAMINATION | EXAMINATION ID NUMBER : |
| | MODALITY : |
| | EXAMINED REGION : |
| | EXAMINATION PROCEDURE : |
| | DATE OF EXAMINATION : 1990. 1.22 |
| | EXAMINATION REQUESTING DEPARTMENT : |
| | EXAMINATION REQUESTING DOCTOR : |
| | NUMBER OF IMAGES : 2 |
| IMAGE | FIRST IMAGE — IMAGE NUMBER : 1 / IMAGING DIRECTION : |
| | SECOND IMAGE — IMAGE NUMBER : 2 / IMAGING DIRECTION : |

| PATIENT | PATIENT NAME | : T. SUZUKI |
| | PATIENT ID NUMBER | : 870802 |
| | DATE OF BIRTH | : 1952. 8. 6 |
| | SEX | : MALE |
| EXAMINATION | EXAMINATION ID NUMBER | : 103541 |
| | MODALITY | : X-RAY |
| | EXAMINED REGION | : CHEST |
| | EXAMINATION PROCEDURE | : PLAIN |
| | DATE OF EXAMINATION | : 1990. 1.22 |
| | EXAMINATION REQUESTING DEPARTMENT | : INTERNAL MEDICINE |
| | EXAMINATION REQUESTING DOCTOR | : M. TANAKA |
| | NUMBER OF IMAGES | : 2 |
| IMAGE | FIRST IMAGE | IMAGE NUMBER : 1 |
| | | IMAGING DIRECTION : P TO A |
| | SECOND IMAGE | IMAGE NUMBER : 2 |
| | | IMAGING DIRECTION : R TO L |

PATIENT INFORMATION

PATIENT NAME : T. SUZUKI
DATE OF BIRTH : 1952. 8. 6
SEX : MALE

EXAMINATION HISTORY

| NO. | REGION | MODALITY | PROCEDURE | DATE OF EXAMINATION | REQUESTING DEPARTMENT | REQUESTING DOCTOR | NO. OF IMAGES |
|---|---|---|---|---|---|---|---|
| ★1 | CHEST | X-RAY | PLAIN | 1990. 1. 22 | INTERNAL MEDICINE | M. TANAKA | 2 |
| 2 | RIGHT FOOT | X-RAY | PLAIN | 1990. 1. 17 | ORTHOPEDIC SURGERY | K. SAITO | 3 |
| ☆3 | CHEST | X-RAY | PLAIN | 1990. 1. 12 | INTERNAL MEDICINE | M. TANAKA | 2 |
| 4 | BRAIN | CT | CONTRAST MEDIUM ADMINISTERED | 1989. 4. 15 | NEUROSURGERY | S. KIMURA | 20 |

FIG. 20

| FINDING NO. | TYPE OF ABNORMALITY | AREA CONTAINING AN ABNORMALITY | RESULT OF COMPARING WITH A PREVIOUS IMAGE | IMAGE NO. IN AN INTERPRETATION EXAMINATION | EXAMINATION ID NO. RELATIVE TO A PREVIOUS IMAGE COMPARED | IMAGE NO. OF A PREVIOUS IMAGE COMPARED |
|---|---|---|---|---|---|---|
| 1 | | | | | | |
| 2 | | | | | | |

CONCLUSION :

(TERMINOLOGY DISPLAY AREA)

FIG.21

| FINDING NO. | TYPE OF ABNORMALITY | AREA CONTAINING AN ABNORMALITY | RESULT OF COMPARING WITH A PREVIOUS IMAGE | IMAGE NO. IN AN INTERPRETATION EXAMINATION | EXAMINATION ID NO. RELATIVE TO A PREVIOUS IMAGE COMPARED | IMAGE NO. OF A PREVIOUS IMAGE COMPARED |
|---|---|---|---|---|---|---|
| 1 | INTERSTITIAL LUNG DISEASE | RIGHT INFERIOR LUNG FIELD | IN PROGRESS | 1 | 100902 | 1 |
| 2 | ENLARGED CARDIAC SHADOW | HEART | ONSET | 1 | 100902 | 1 |
|   |   |   |   |   |   |   |

FIG.22

| FINDING NO. | TYPE OF ABNORMALITY | AREA CONTAINING AN ABNORMALITY | RESULT OF COMPARING WITH A PREVIOUS IMAGE | IMAGE NO. IN AN INTERPRETATION EXAMINATION | EXAMINATION ID NO. RELATIVE TO A PREVIOUS IMAGE COMPARED | IMAGE NO. OF A PREVIOUS IMAGE COMPARED |
|---|---|---|---|---|---|---|
| 1 | INTERSTITIAL LUNG DISEASE | RIGHT INFERIOR LUNG FIELD | IN PROGRESS | 1 | 100902 | 1 |
| 2 | ENLARGED CARDIAC SHADOW | HEART | ONSET | 1 | 100902 | 1 |
|  |  |  |  |  |  |  |

CONCLUSION :

CAD POINTS OUT AN ABNORMALITY CHANGE UNFOUND IN THE FINDINGS.

FIG.23

MEDICAL INFORMATION PROCESSING SYSTEM FOR SUPPORTING DIAGNOSIS

This application is a Continuation of application Ser. No. 07/880,522, filed on May 8, 1992, now abandoned.

BACKGROUND OF THE INVENTION

1. Field of the Invention

The present invention relates to a medical information processing system for comparing a plurality of diagnostic information including doctors' findings and results of computerized analysis of images and other examination data and thus supporting doctors in evaluating examination data more efficiently.

2. Discussion of the Background

At many medical institutes, images (one of examination data) are evaluated as described below.

First, a doctor of an examination requesting department (for example, Department of Internal Medicine) requests, for example, the Department of Radiology to examine a patient (by performing radiography, CT, or other diagnostic imaging). This request is performed by issuing an examination request sheet in which the following items are written:

(a) Patient information: patient ID number, patient name, date of birth, and sex (b) Examination requester information: examination requesting department, examination requesting doctor name (c) Contents of an examination: modality (for example, X-ray,CT), region, and procedure (d) Others: purpose of examination, and clinical information Next, a radiologic technologist, for example, examines the patient according to the contents of the examination request sheet, then develops exposed films.

Then, an interpreting doctor (for example, a radiologist) interprets examination images on developed films. At this time, the patient's previous images are often referenced. This is very important to improve quality of interpretation. The interpreting doctor works out an interpretation report after completing interpretation. Information the interpreting doctor writes in the interpretation report includes findings from interpretation, a conclusion, his/her name, and a date of interpretation.

Finally, the interpretation report is submitted to the examination requesting doctor.

Unlike analog images on films, digital images do not deteriorate in image quality after they are copied or as time passes. Moreover, the digital images simplify computerized image processing. These features facilitate attempts of analyzing digital images using a computer to detect patient abnormalities. This has born fruit. The technology is referred to as computer-aided diagnosis (hereafter, CAD), which is expected to further improve accuracy in evaluating images and reduce a load to a doctor in evaluating images.

An algorithm for detecting patient abnormalities in CAD has been introduced in, for example, the following literatures:

(a) Katsuragawa S. et al. Image Feature Analysis and Computer-aided Diagnosis in Digital Radiography: Classification of Normal and Abnormal Lungs with Interstitial Diseases in Chest Images. Medical Physics 1989; 16: 38–44.

(b) Giger M. L. et al. Image Feature Analysis and Computeraided Diagnosis in Digital Radiography: Automated Detection of Nodules in Peripheral Lung Fields. Medical Physics 1988; 15(3): 158–166.

(c) Chan H. P. et al. Image Feature Analysis and Computeraided Diagnosis in Digital Radiography: Automated Detection of Microcalcifications in Mammography. Medical Physics 1987; 14(1): 538–548.

(d) Doi K. et al. Possibility of Computer-aided Diagnosis in Digital Radiography. Nippon Acta Radiologica 1989; 45(5): 653–663.

The technologies to be implemented in a system for detecting abnormalities by means of CAD have been disclosed in the following literatures:

(a) Japanese Patent Laid-Open No. 2-185240
(b) Japanese Patent Laid-Open No. 2-152443
(c) Japanese Patent Laid-Open No. 1-125675

With the progress of digitized imaging, a picture archiving and communication system (hereafter, PACS) has been used to evaluate images in recent years. The PACS stores, communicates, and displays images (X-ray, CT, MR, and other digital images), thus assisting doctors in observing images.

The PACS stores image data sent from X-ray, CT, MRI, and other imaging systems in a database, and transfers required image data from a database to an image workstation. The image workstation displays received image data on its cathode ray tube (hereafter, CRT). Then, a doctor interprets images displayed on the workstation, evaluates the images, and then creates an interpretation report. The interpretation report can be created on and stored in the PACS.

The PACS obviates searching for medical image films (analog images), carrying films, and hooking and unhooking films on a film viewer.

Many technologies concerning the system configuration and functions of a PACS have been disclosed and detailed in:

(a) Japanese Patent Laid-Open No. 62-121576
(b) Japanese Patent Laid-Open No. 63-10269
(c) Japanese Patent Laid-Open No. 64-13837
(d) Japanese Patent Laid-Open No. 64-17154
(e) Japanese Patent Laid-Open No. 2-103668
(f) Japanese Patent Laid-Open No. 2-119840

As described above, both CAD and a PACS are available these days.

However, a system integrating both the CAD and PACS has not been developed. Therefore, the advantages of the CAD and PACS cannot be simultaneously exploited in clinical practice.

For example, in many cases, it is required to apply CAD to previous examination images acquired for a certain period of time and thus to diagnose whether a lesion is in progress or recovered.

However, when a great number of previous examination images must be handled, it is time-consuming to load the examination images into a PACS workstation. This requires a memory having a very large capacity inside the workstation, deteriorating use efficiency of the PACS.

To load examination images into a predetermined workstation of a PACS, the workstation must issue a request to a database. Therefore, it is time-consuming to load all the examination images into the workstation.

CAD is proceeded independently of PACS-based interpretation of examination images. When a doctor tries to reference CAD results and interpret examination images or when a doctor wants to compare his/her own results of interpretation with the CAD results, very complex operations are awaited.

When medical images stored in a database of PACS are sent from the database to a workstation and displayed on a plurality of CRT's of the workstation, the images are displayed in order of arriving at the workstation.

Therefore,when a doctor interprets the medical images using the workstation of PACS,the images are not displayed frequently in a display position according to predetermined rules.

Thus,the doctor must replace the images which are displayed on each of the CRT of the workstation so that the images are displayed at the predetermined position.

Japanese patent laid-Open no.1-296383 discloses a display system comprising detecting means for detecting a modality of each image from the image, categorizing means for categorizing the images according to the modality, determinating means for determining an image displaying order using the category and displaying means for displaying the images on a monitor in the displaying order.

The display system can determine an order in which images are displayed, and display the images sequentially on a monitor according to the order, but can't display the images simultaneouly on a plurality of monitors.

SUMMARY OF THE INVENTION

The object of the present invention is to provide a medical information processing system capable of integrating a CAD function and a PACS into a single system.

Another object of the invention is to provide a medical information processing system capable of loading previous examination data into workstations efficiently.

Another object of the invention is to provide a medical information processing system capable of automatically loading examination data to be interpreted into workstations.

Another object of the invention is to provide a medical information processing system capable of comparing results of a doctor's interpretation or findings with CAD results, calling doctor's attention if the results are inconsistent, and outputting the contents of the inconsistency.

Another object of the invention is to provide a display system capable of displaying a plurality of medical examination images in predetermined relative positions so that a doctor can observe the images efficiently and thereby facilitating an interpretation and a diagnosis for images.

Another object of the invention is to provide a display system capable of automatically detecting an imaging direction or a modality of an image so that a doctor doesn't have to input the imaging direction or the modality.

Another object of the invention is to provide a display system capable of automatically inputting an imaging direction and a modality of an image and storing the imaging direction and the modality in the light of additional information.

According to the present invention, a medical information processing system comprises data loading means for loading examination data including at least one of interpretation data used for interpretation and interpretation reference data to be referenced during interpretation, said data loading means includes workstation means for loading said examination data and said data loading means selects said interpretation reference data according to a predetermined order and then loads the selected interpretation reference data into said workstation means.

Thereby, interpretation reference data having a high possibility of being referenced can be loaded into the workstation in a preferred manner. This realizes efficient interpretation.

According to a medical information processing system of the present invention, the workstation means comprises a plurality of workstations and the data loading means has a memory containing workstation vs. interpretation examination modality information which associates said interpretation data with said workstations and said data loading means selects a workstation into which said interpretation data is loaded, from said workstations according to said workstation vs. interpretation examination modality information and then loads said interpretation data and said interpretation reference data into said workstation selected.

Thereby, a workstation into which examination images are loaded can be determined automatically. This contributes to quick setup for interpretation.

According to the present invention, a medical information processing system comprises data loading means for loading examination data including at least one of interpretation data used for interpretation and interpretation reference data to be referenced during interpretation; diagnostic information creating means for creating diagnostic information relative to said loaded examination data; diagnostic information comparing means for comparing said diagnostic information with each other; and diagnostic information output means for outputting at least one of said created diagnostic information or the results of comparing said diagnostic information.

Thereby, doctor's findings and outputs of CAD results can be displayed in comparison. This facilitates efficiency in interpreting examination images.

According to a medical information processing system of the present invention, the diagnostic information creating means includes computerizing means for creating diagnostic information relative to at least one of said interpretation data and said interpretation reference data.

Thereby, accurate diagnosis can be made by using CAD.

According to a medical information processing system of the present invention, the computerizing means calculates said positions of abnormalities in association with image areas of said interpretation data or said interpretation reference data and outputs the calculated positions of abnormalities as locations in an image in which said diagnostic information is displayed.

This facilitates efficiency in understanding the states of lesions.

According to a medical information processing system of the present invention, the diagnostic information comparing means compares said diagnostic informations with each other.

Therefore, the progresses of lesions estimated by CAD can be displayed.

According to a medical information processing system of the present invention, the diagnostic information creating means includes computerizing means for creating diagnostic information relative to at least one of said interpretation data or said interpretation reference data and said diagnostic information comparing means compares first diagnostic information created as findings with second diagnostic information said computerizing means creates.

Thereby, the results of a doctor's interpretation can be checked effortlessly in comparison with CAD results. This improves interpretation accuracy.

According to a medical information processing system of the present invention, the diagnostic information output means outputs a predetermined content when said first diagnostic information is inconsistent with said second diagnostic information.

This allows a doctor to find a lesion he/she might have missed, thus improving interpretation accuracy.

According to the present invention, a display system comprises display means for displaying a plurality of examination datas, display position determining means for automatically determining relational positions in which the examination datas are displayed on the display means, according to a predetermined relational information. Thereby,a doctor need not replace a plurality of datas after the datas are displayed on the monitors. This ommits a replacing operation,and realizes efficient observation, interpretation and diagnosis for medical images.

According to a display system of the invention, the relational information includes an information relating the relational positions to an imaging direction and a modality of each image. Thereby,a doctor observe the medical datas efficiently.

According to the present invention, a data acquisition apparatus comprises information input means for inputting an information including an imaging direction or a modality of an examination image data. Thereby,an operator can input the information including the imaging direction and the modality of each image. Therefore a workstation can receive the images and their information from the image acqusition system and then using the information, can display the images on monitors of the workstation in a display position decided on the imaging direction and modality of the image.

According to the present invention,a data acquisition apparatus comprises information deciding means for automatically deciding an information including an imaging direction or a modality of an examination image data by analyzing each data.Thereby, an operator doesn't have to input the information including the imaging direction and modality. Therefore, a workstation can receive the images and their information from the image acqustion system, and then using the information, can display the images on monitors of the workstation in a display position decided on the imaging direction and modality of the image.

BRIEF DESCRIPTION OF THE DRAWINGS

FIG. 15 shows an example of information displayed on a screen of the display of a film digitizer after film densities are digitized;

FIG. 16 shows an example of information displayed on a screen of the display of a film digitizer when an operator has completed entering necessary data after film density digitization;

FIG. 20 shows an example of an examination history displayed on the character display of a workstation during interpretation;

FIG. 21 shows an example of a format of an interpretation report displayed on the character display of a workstation;

FIG. 22 shows an example of findings entered during creation of an interpretation report and displayed on the character display of a workstation;

FIG. 23 shows an example of a message to an interpreting doctor displayed on an interpretation report creation screen of the character display of a workstation.

DESCRIPTION OF PREFERRED EMBODIMENTS

An embodiment of a medical information processing system according to the present invention will be described in conjunction with the appended drawings.

In the embodiment below, the present invention applies to a PACS. However, the medical information processing system of this invention is not restricted to the PACS but can apply to all systems among which medical data is interchangeable over a network.

In the embodiment below, the chest is chosen as a diagnostic region and plain chest X-ray images are specified as a type of images evaluated. However, the present invention is not limited to the region and the type of image but can apply to various regions and types of images.

Figure 1:
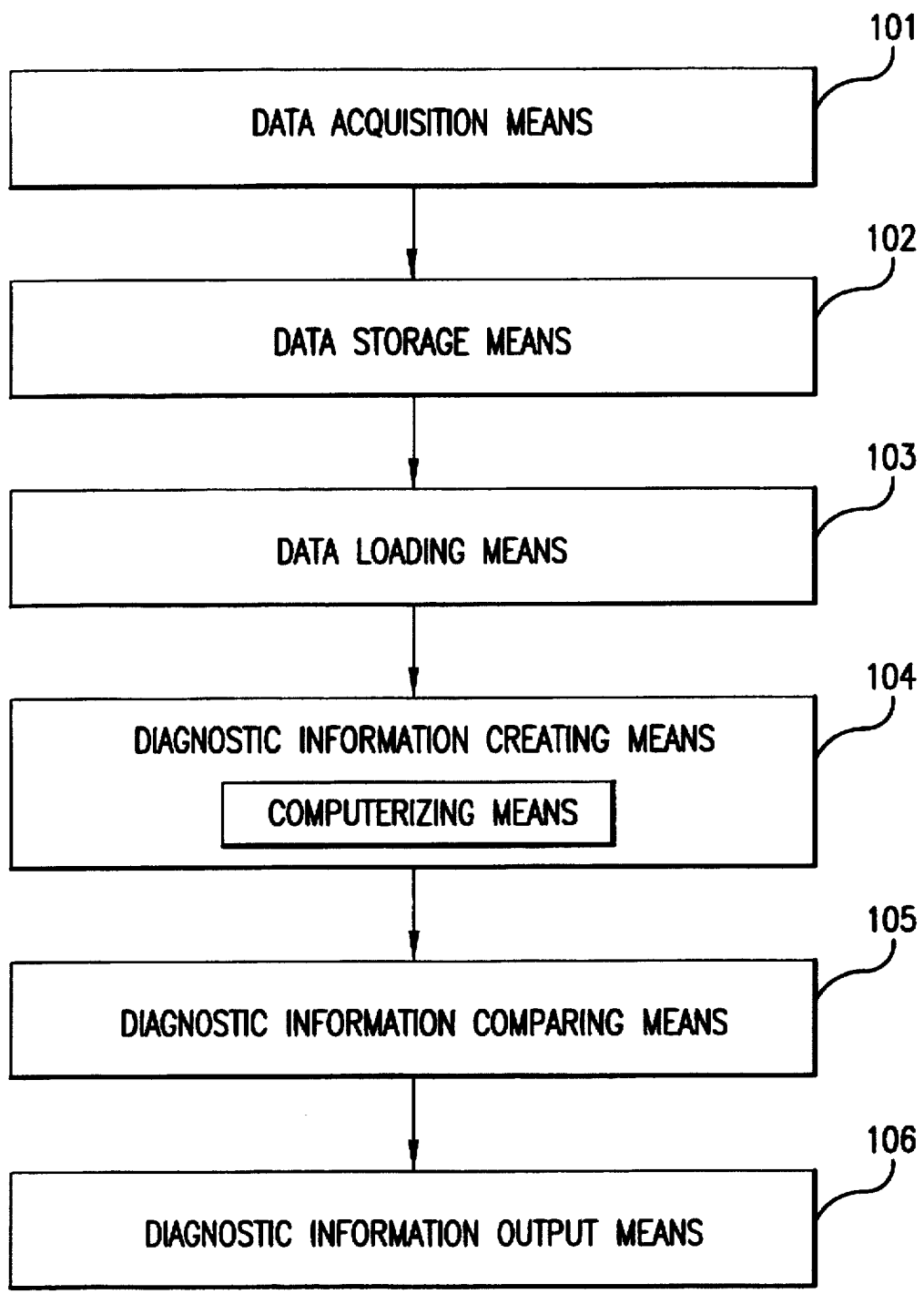
FIG. 1 is a block diagram of a medical information processing system of the embodiment.

FIG. 1 is a block diagram of an entire medical information processing system of the prevent invention.

As shown in FIG. 1, a medical information processing system of the invention comprises data acquisition means 101, that is, modalities for acquiring examination data to be evaluated, data storage means 102 for storing the acquired examination data, data loading means 103 for loading the examination data, diagnostic information creating means 104 for creating diagnostic information concerning the loaded examination data, diagnostic information comparing means 105 for comparing diagnostic information each other, and diagnostic information output means 106 for outputting at least either the created diagnostic information or the results of comparing diagnostic information.

Figure 2:
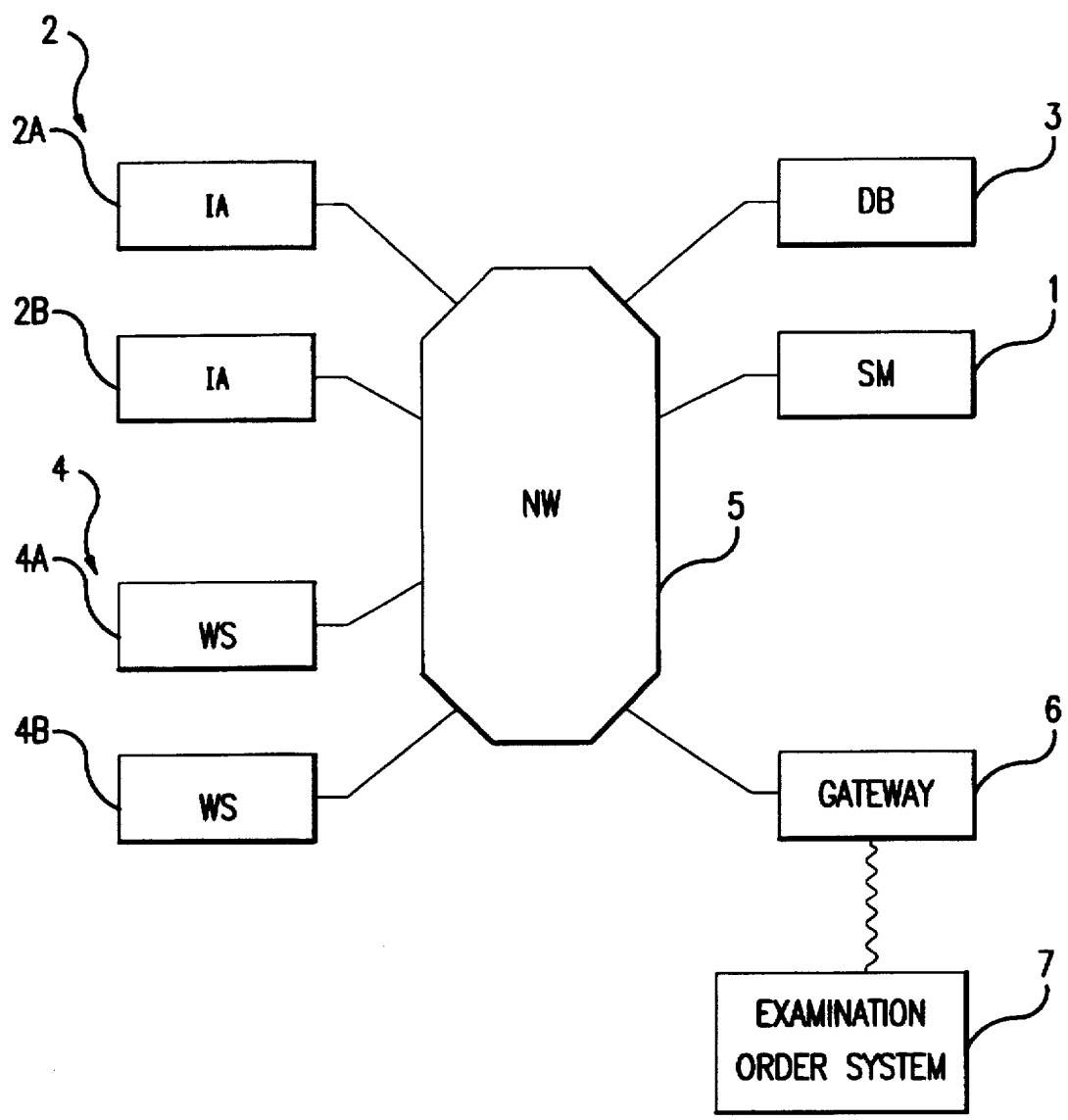
FIG. 2 is a system configuration diagram of a PACS.

FIG. 2 shows an example of applying a medical information processing system of the prevent invention to a PACS.

The data acquisition means 101 includes image acquisition apparatuses (IA) 2 for acquiring examination images serving as examination data according to examination request information a system manager 1 receives. The data storage means 102 is included in a database 3 for storing acquired examination images.

The data loading means 103 loads stored examination images into a workstation (WS) 4 over a network 5. The data loading means 103 is formed by a combination of the system manager 1, the control part of the database 3, and the control part of the workstation 4.

The diagnostic information creating means 104 which is arranged in the workstation 4, creates diagnostic information relative to the examination images loaded in the workstations 4 as findings, inputs the created diagnostic information to the workstation 4, and allows the workstation 4 to create diagnostic information automatically.

The diagnostic information comparing means 105 which is also arranged in the workstation 4, compares the diagnostic information created as findings with the diagnostic information the workstation creates, or mutually compares the diagnostic information the workstation creates.

The diagnostic information output means 106 which is also arranged in the workstation 4, outputs at least either the created diagnostic information or the results of comparing diagnostic information to a display of the workstation 4.

The system manager (SM) 1 receives examination request information from an examination order system 7 via a gateway 6.

The image acquisition apparatus (IA) 2 may be, for example, a film digitizer, a diagnostic X-ray apparatus, an X-ray CT apparatus, or an MRI apparatus. Multiple image acquisition apparatuses, for example, represented as 2A and 2B in FIG. 2, can be connected on a network (NW) 5, regardless of the type of modality.

The database (DB) 3 stores digital images the image acquisition apparatuses (IA) 2 generate, and includes low-speed media (for example, optical disks) and high-speed media (for example, magnetic disks).

Similarly to image acquisition apparatuses 2, multiple workstations (WS) 4, for example, represented as 4A and 4B in FIG. 2, can be connected on the network (NW) 5.

The network (NW) 5 serves as transmission paths for commands and data communicated among components. Optical fibers are used as transmission media.

The network 5 is formed as a ring local area network. A star or other network can also be used.

Figure 3:
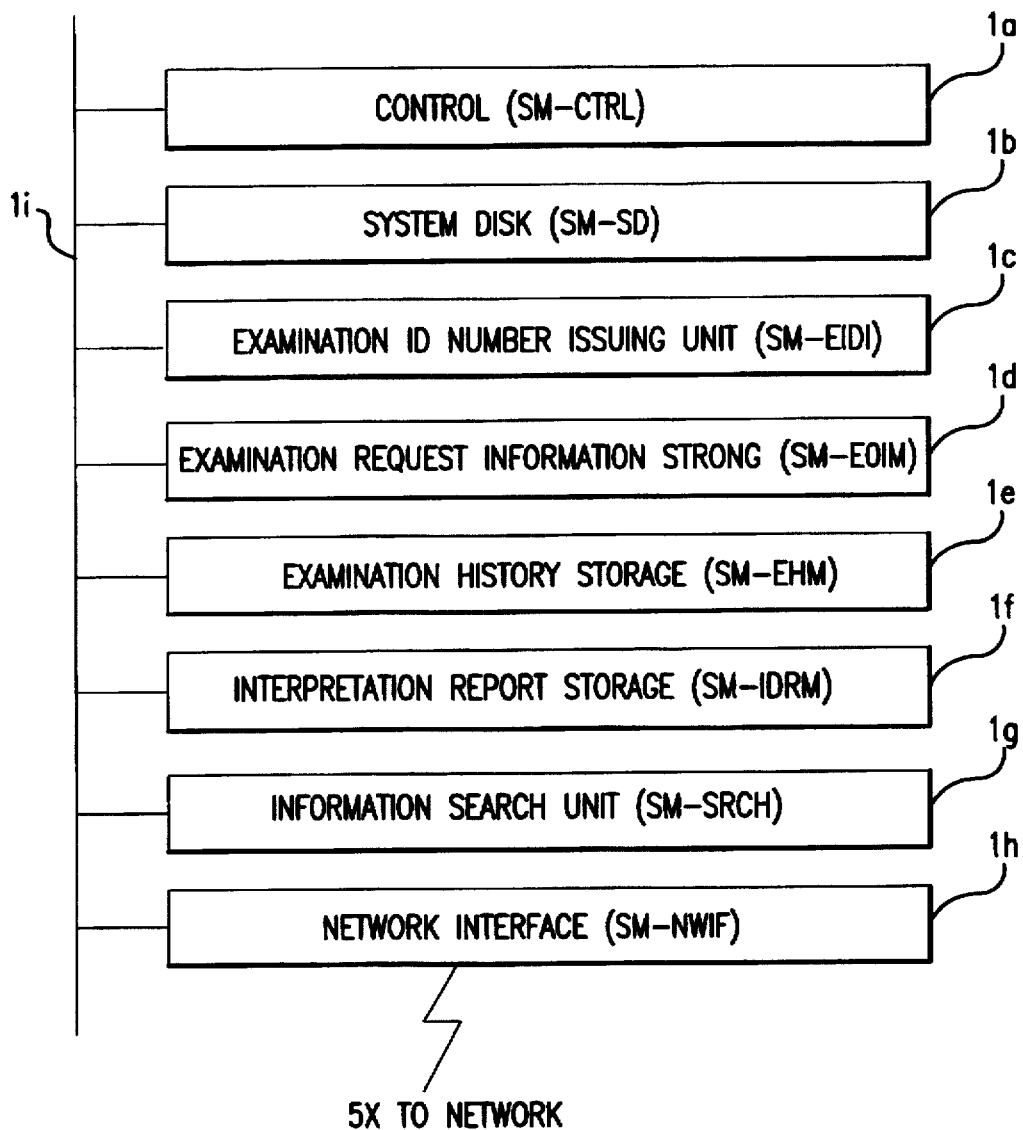
FIG. 3 is a configuration diagram of a system manager.

FIG. 3 is a detailed block diagram of the system manager (SM) 1.

The system manager 1 comprises:

a control (SM-CTRL) 1a receiving examination request information from an examination order system 7 via a gateway 6 and being capable of controlling the operation of the entire system manager 1;

a system disk (SM-SD) 1b for storing various data or programs;

an examination ID number issuing unit 1c for issuing an examination ID number on receipt of examination request information;

an examination request information storage 1d for storing the examination request information and examination ID numbers;

an examination history storage 1e for storing patients' examination histories;

an interpretation report storage 1f for storing interpretation reports; and an information search unit (SM-SRCH) 1g for searching storages according to a designated keyword in response to an instruction from the control 1a and writing the result of search in memory of the control 1a.

The system manager 1 further comprises a network interface (SM-NWIF) 1h for communicating with other subsystems over the network 5 and a control bus (SM-CBUS) 1i serving as a transmission path for various control information and data within the system manager 1.

The control 1a comprises a central processing unit (hereafter, CPU) and a system memory (semiconducting memory), which receives, as described above, examination request information.

Table 1 below lists the data items included in the examination request information.

TABLE 1

Example of data items included in examination request information

Patient ID number
Patient name
Date of birth
Sex
Modality
Region to be examined
Examination procedure
Examination requesting department
Examination requesting doctor
Date of examination request
Requested date of examination
Requested time of examination
Purpose of examination
Patient clinical information
Disclosed diseases
⋮
⋮
⋮

The system disk (SM-SD) 1b stores, as described above, various data or programs together with programs for operating the system manager 1. These data and programs are read out when the power supply of the system manager 1 is turned on, then written in system memory of the control 1a.

The data loading means 103 of the present invention fetches interpretation data or data to be interpreted from among examination data stored in a database 3, then loads the interpretation data into the workstation 4. The data loading means 103 also selects interpretation reference data or data to be referenced during interpretation according to a predetermined order, then loads the selected interpretation reference data into the workstation 4.

The predetermined order is determined according to interpretation reference priority information created using interpretation reference data loading rule information which defines priorities in terms of at least one of the examined region, modality, and date of examination specified in interpretation reference data.

The interpretation reference data loading rule information indicates attributes of previous examination images to be referenced according to a predetermined priority order.

Table 2 lists general data items included in the interpretation reference data loading rule information which are used to instruct the database (DB) 3 to load previous images of a specific patient.

TABLE 2

Example of data items included in interpretation
reference data loading rule information Attribute 1 of a previous image referenced during
interpretation (first priority)
Attribute 2 of a previous image referenced during
interpretation (second priority)

TABLE 2-continued

Example of data items included in interpretation
reference data loading rule information

⋮

Attribute N of a previous image referenced during
interpretation (N-th priority)

In Table 2, images given higher priorities have greater possibilities of being referenced during interpretation.

The interpretation reference data loading rule information can be rewritten any time.

Table 3 lists specific data values of interpretation reference data loading rule information of this embodiment in a listing form.

TABLE 3

Example of data values of interpretation
reference data loading rule information Attribute 1 of a previous image referenced during
interpretation (first priority) [Examination of the same
region to be examined]
Attribute 2 of a previous image referenced during
interpretation (second priority) [Examination of the same
modality]
Attribute 3 of a previous image referenced during
interpretation (third priority)
[Examination of a latest date of examination]

The data values in FIG. 3 represent rules below. That is to say:

(a) The first priority is given to an examination of the same region as, the same modality as, and a later date of examination than, an interpretation examination.

(b) The second priority is given to an examination of the same region as, the same modality as, and an earlier date of examination than, an interpretation examination.

(c) The third priority is given to an examination of the same region as, a different modality from, and a later date of examination than, an interpretation examination.

(d) The fourth priority is given to an examination of the same region as, a different modality from, and an earlier date of examination than, an interpretation examination.

(e) The fifth priority is given to an examination of a different region from, the same modality as, and a later date of examination than, an interpretation examination.

(f) The sixth priority is given to an examination of a different region from, the same modality as, and an earlier date of examination than, an interpretation examination.

(g) The seventh priority is given to an examination of a different region from, a different modality from, and a later date of examination than, an interpretation examination.

(h) The eighth priority is given to an examination of a different region from, a different modality from, and an earlier date of examination than, an interpretation examination.

The data loading means 103 of the present invention selects a workstation, into which interpretation data and interpretation reference data are loaded, according to workstation vs. interpretation examination modality information which associates interpretation data with workstations 4, then loads interpretation data and interpretation reference data into the selected workstation 4.

Table 4 shows a specific example of workstation vs. interpretation examination modality information.

TABLE 4

Example of workstation vs. interpretation
examination modality information

| Workstation ID | Interpretation examination modality |
|---|---|
| WS-1 | X-ray |
| WS-2 | X-ray |
| WS-3 | CT |
| WS-4 | MRI |
| ⋮ | ⋮ |

In this embodiment, as shown in Table 4, workstations display examination images of specific modalities during interpretation.

For example, a workstation having an ID of WS-1 displays X-ray images alone as far as uninterpreted images are concerned.

However, when it comes to patient's previous images, images of any modality can be referenced.

The workstation vs. interpretation examination modality information can also be rewritten.

The interpretation reference data loading rule information and workstation vs. interpretation examination modality information should be stored on, for example, a system disk 1b.

The examination ID number issuing unit (SM-EIDI) 1c issues, as described previously, an examination ID number on receipt of new examination request information in such a way that examination ID numbers will be mutually different within the system.

Assuming that the initial value of an examination ID number is 0 and a control (SM-CTRL) 1a instructs issuance of an examination ID number, the examination ID number issuing unit 1c increments the examination ID number by 1, then returns a new examination ID number to the control 1a.

Therefore, in the aforesaid example, the examination ID number starts with 1.

The examination request information storage (SM-EOIM) 1d can, as described previously, store examination request information sent from the examination order system 7 together with an examination ID number, which is, for example, formed with a magnetic disk.

Table 5 lists the data items stored in the examination request information storage 1d in a listing form.

TABLE 5

Example of data items stored in the examination
request information storage of the system manager Examination ID number
Patient ID number
Patient name
Date of birth
Sex
Modality
Examined region
Examination procedure
Examination requesting department
Examination requesting doctor
Date of examination request
Required date of examination
Required time of examination
Purpose of examination
Patient clinical information TABLE 5-continued Example of data items stored in the examination
request information storage of the system manager Disclosed diseases
:
:

The above data items outnumbers those of examination request information listed in Table 1 by one item or an examination ID number.

The examination history storage (SM-EHM) 1e can, as described above, store patient examination histories, and is formed with, for example, a magnetic disk.

Table 6 lists the data items included in a patient's examination history in a listing form.

TABLE 6

Example of data items included in a patient's examination history

Patient information

Patient ID number
Patient name
Date of birth
Sex
Information concerning the first examination Examination ID number
Modality
Examined region
Examination procedure
Examination requesting department
Examination requesting doctor
Date of examination
Number of images
:
:
Information concerning the N-th examination Examination ID number
Modality
Examined region
Examination procedure
Examination requesting department
Examination requesting doctor
Date of examination
Number of images The interpretation report storage (SM-IDRM) 1f stores, as described above, interpretation reports, and is formed with, for example, a magnetic disk.

Table 7 lists the data items included in an interpretation report in a listing form.

TABLE 7

Example of data items included in an interpretation report

Patient information

Figure 4:
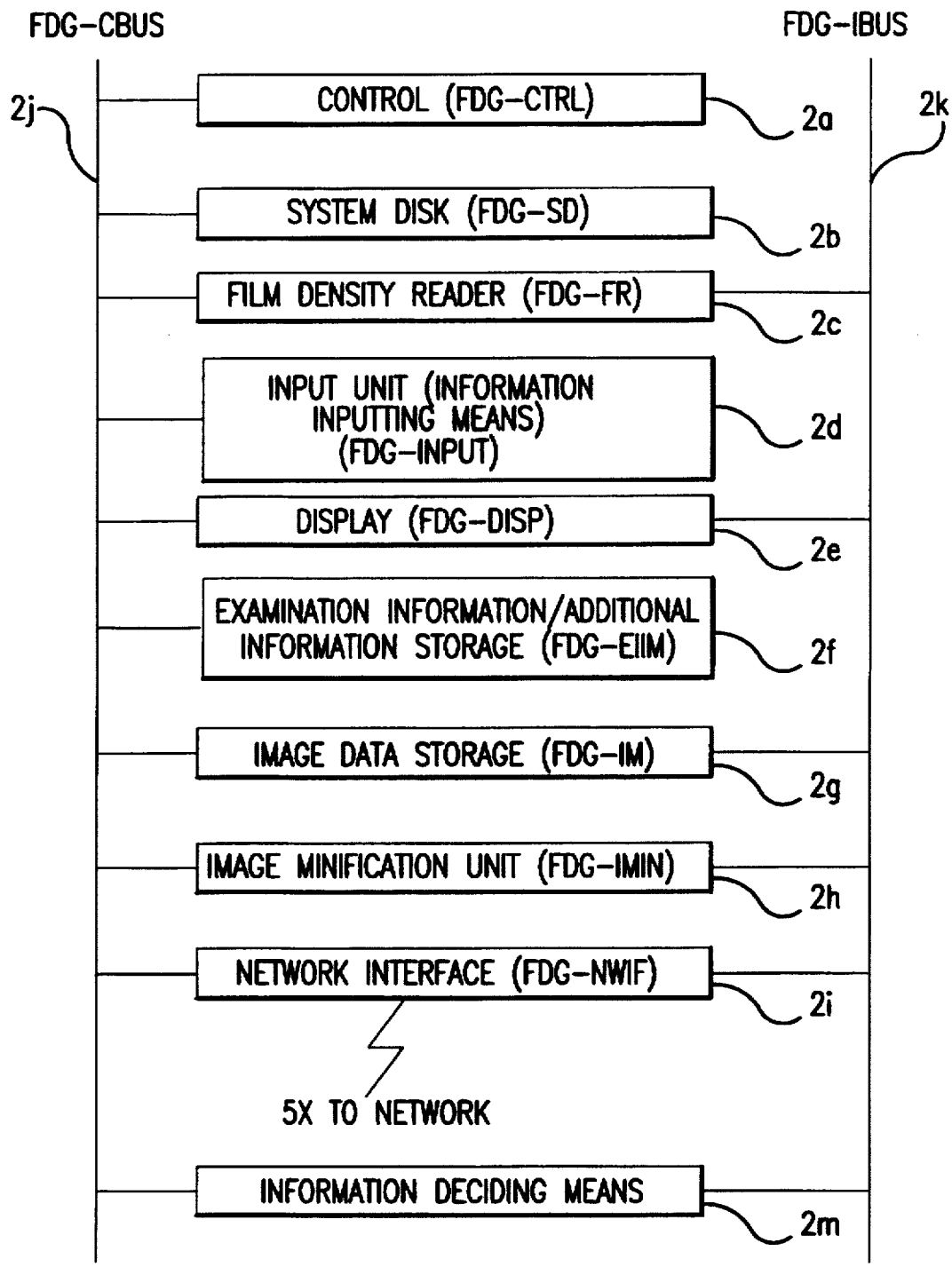
FIG. 4 is a configuration diagram of a film digitizer.

Patient ID number
Patient name
Date of birth
Sex
Information concerning the examination Examination ID number
Modality
Examined region
Examination procedure
Examination requesting department
Examination requesting doctor TABLE 7-continued Example of data items included in an interpretation report Date of examination
Interpreting doctor
Findings Finding 1
Finding 2
:
:
Finding N
Conclusion FIG. 4 is a detailed block diagram of a film digitizer (FDG) serving as an image acquisition apparatus 2 which is, hereafter, represented as 2.

The film digitizer (FDG) 2 comprises:

a control (FDG-CTRL) 2a requesting the system manager (SM) 1 to transfer examination request information, receiving examination request information, and being capable of controlling the entire film digitizer 2;

a film density reader (FDG-FR) 2c for reading film densities of X-ray films and generating digital images;

an input unit 2d for inputting examination information or additional information;

a display 2e for displaying the information;

an examination information/additional information storage 2f for storing the information; and an image data storage 2g for temporarily storing image data.

The film digitizer 2 further comprises a system disk (FDG-SD) 2b containing programs for operating the film digitizer 2, an image minification unit (FDG-IMIN) 2h for minifying the matrix sizes of digitized images, a network interface (FDG-NWIF) 2i for communicating with other subsystems over a network 5, a control bus (FDG-CBUS) 2j serving as a transmission path for various control information within the film digitizer 2, and an image bus (FDG-IBUS) 2k serving as a transmission path for image data within the film digitizer 2.

The film digitizer 2 has a built-in clock, which is not shown in FIG. 4, for referencing times and dates indicated digitally.

The control (FDG-CTRL) 2a comprises a CPU and a system memory (semiconducting memory).

The system disk (FDG-SD) 2b is formed with, for example, a magnetic disk. When the power supply of the film digitizer 2 is turned on, programs stored in the system disk 2b are read, then written in system memory of the control 2a.

The film density reader (FDG-FR) 2c, as described above, optically reads densities of an image on film, then digitizes the image.

A single film is digitized as a single image. The matrix size of a digitized image is 2048 by 2048 pixels. One pixel is ten bits long.

Figure 5:
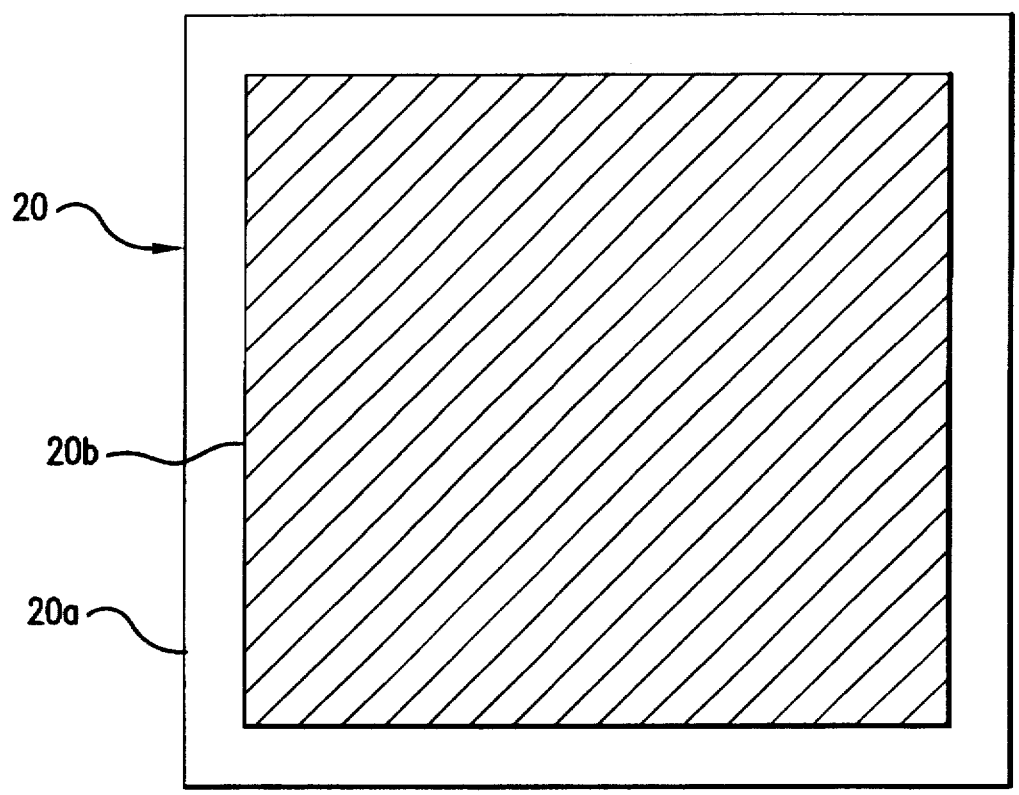
FIG. 5 shows the relationships between a film size and a film density read-out area.

The film density reader 2c has a mechanism for automatically detecting film sizes. According to a film size, a pixel size is specified automatically. For example, when a film is 14 by 14 inches (35.56 by 35.56 cm) in size, the size of a pixel is set to 0.016 by 0.016 cm. The product of the pixel size (0.016 cm) by the matrix size (2048) disagrees with the film size (35.56 cm). This is because, as shown in FIG. 5, a film 20 includes an edge 20a from which densities are not read (a hatched area 20b represents a film density read-out area).

The input unit (FDG-INPUT) 2d is, as described above, means for inputting examination information or additional information, and formed with a keyboard or a touch-sensitive screen.

Herein, examination information represents information describing an examination and is appended to each examination. Table 8 lists the data items included in examination information in a listing form.

TABLE 8

Example of data items included in examination information

Examination ID number
Patient ID number
Patient name
Date of birth
Sex
Modality
Examination region
Examination procedure
Examination requesting department
Examination requesting doctor
Date of examination
Number of images
:
:

Additional information represents information describing an image and is appended to each image. Table 9 lists the data items included in additional information in a listing form.

TABLE 9

Example of data items included in additional information

Figure 6:
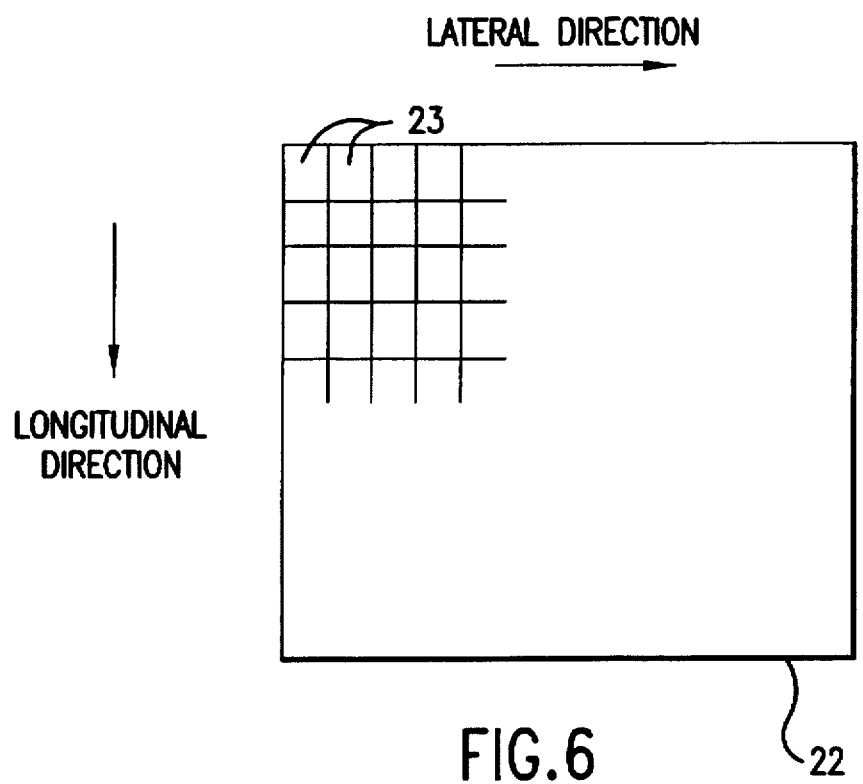
FIG. 6 shows the relationships between an image and pixels.
Figure 7:
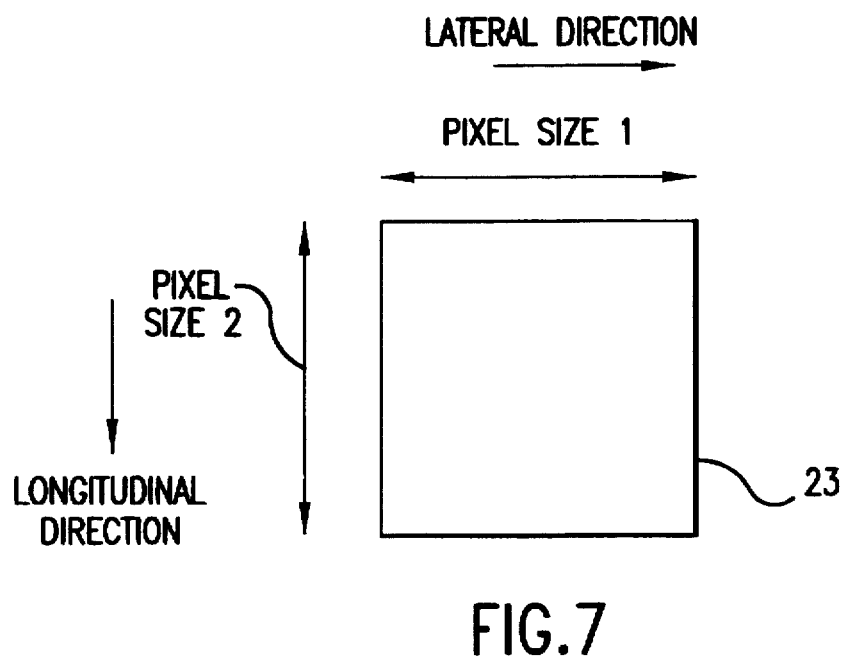
FIG. 7 shows the relationships between pixels and pixel sizes.

Examination ID number
Image number (image number within the examination)
Pixel size 1 (lateral length of pixels)
Pixel size 2 (longitudinal length of pixels)
Matrix size 1 (number of pixels in lateral direction)
Matrix size 2 (number of pixels in longitudinal direction)
Pixel bit length
Amount of data
Imaging direction
:
:

FIG. 6 shows the relationships between an image and pixels, and FIG. 7, the meanings of the pixel size 1 and pixel size 2 listed in Table 9. That is to say, an image 22 of FIG. 6 is made up of multiple pixels 23 arranged sideways and lengthwise. The lateral length of pixels 23 is represented as the pixel size 1, and the longitudinal length, the pixel size 2.

Part of the additional information is generated automatically by the film digitizer 2. The data items and the determinations of the values are as follows:

(a) Image number

Image numbers are determined in the order in which the images are digitized. For example, a digitized image of the N-th film is assigned an image number N.

(b) Pixel size 1 and pixel size 2

As described above, an appropriate value is chosen during digitization. In this embodiment, 0.016 cm is adopted.

(c) Matrix size 1 and matrix size 2

As described above, 2048 is adopted in this embodiment.

(d) Pixel bit length

As described above, 10 is adopted in this embodiment.

(e) Amount of data

An amount of data is determined as a product of a matrix size 1 by a matrix size 2 by a pixel bit length. In this embodiment, it is about 40M bits (=5M bytes).

(f) an imaging direction

The film digitizer 2 as an image acqusition apparatus comprises an information inputting means for inputting an information including an imaging direction and a modality of an examination image data,and the input unit 2d functions as the information inputting means.

Instead of the information inputting means,the film digitizer 2 may comprises an information deciding means 2m for automatically deciding an information including an imaging direction and modality of each image by analyzing each image.

The information deciding means 2m may be provided in the input unit 2d or the examination information/additionnal information storage 2f.

The display (FDG-DISP) 2e displays, as described previously, input information of the film digitizer 2 and digitized images, and is formed with a CRT display or a liquid crystal panel.

The display 2e can display images having a maximum matrix size of 2048 by 2048 pixels.

The examination information/additional information storage (FDG-EIIM) 2f stores, as described previously, examination information and additional information temporarily, and is formed with, for example, a semiconducting memory.

The image data storage (FDG-IM) 2g temporarily stores, as described previously, images the film density reader 2c digitizes, which is formed with, for example, a semiconducting memory.

The image minification unit (FDG-IMIN) 2h can, as described previously, minify matrix sizes of digitized images.

X-ray films are digitized in a 2048 by 2048 matrix size. However, when the images are displayed on the display (FDG-DISP) 2e, multiple images are displayed on a single screen. Therefore, the matrix size is minified to about 512 by 512. Minification is achieved by thinning out data.

Figure 8:
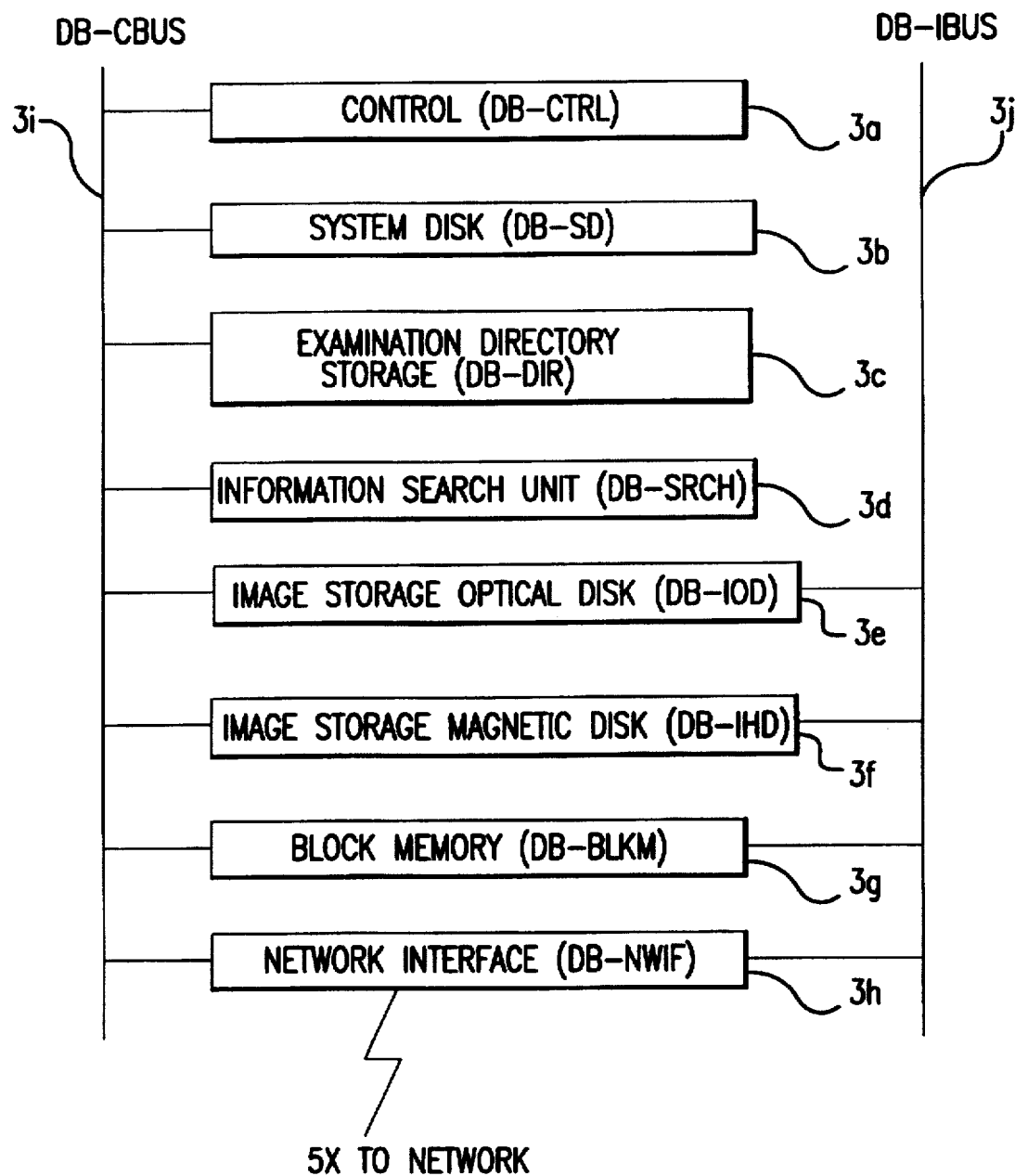
FIG. 8 is a configuration diagram of a database.

FIG. 8 is a detailed block diagram of the database (DS) 3. The database (DS) 3 comprises:

a control (DB-CTRL) 3a capable of controlling the entire database 3;

an examination directory storage 3c for storing examination directories;

an information search unit 3d for searching examination directories;

a long-term storage 3e for storing image data, additional information, and overlay data for a prolonged period;

a temporary storage 3f for temporarily storing image data and additional information sent from the image acquisition apparatus 2, reading out previous reference image data to be referenced during interpretation from the long-term storage in response to a request from a system manager 1, storing the read data, then transferring the data to the workstation 4; and a block memory 3g for temporarily storing image data, examination information, and additional information.

The database 3 further comprises a system disk (DB-SD) 3b capable of storing programs for operating the database 3, a network interface (DB-NWIF) 3h for communicating with other subsystems over a network 5, a control bus (DS-CBUS) 3i serving as a transmission path for various control information within the database 3, and an image bus (DB-IBUS) 3j serving as a transmission path for image data within the database 3.

The control (DB-CTRL) 3a comprises a CPU and a system memory (semiconducting memory).

The system disk (DB-SD) 3b is, for example, a magnetic disk. Programs for operating the database (DB) 3 are read out when the power supply of the database 3 is turned on, then written in system memory of the control 3a.

The examination directory storage (DB-DIR) 3c is formed with, for example, a magnetic disk.

Table 10 lists the data items of directory information for one examination contained in an examination directory.

TABLE 10

Example of data items of directory information
for one examination contained in an examination directory Examination ID number
Patient ID number
Patient name
Date of birth
Sex
Modality
Examined region
Examination procedure
Examination requesting department
Examination requesting doctor
Date of examination
Number of images
  :
  :
Address of additional information of the first image on low-speed medium
Amount of data in additional information of the first image
Address of image data of the first image on low-speed medium
Amount of data in image data of the first image
  :
  :
Address of additional information of the N-th image on low-speed medium
Amount of data in additional information of the N-th image
Address of image data of the N-th image on low-speed medium
Amount of data in image data of the N-th image In Table 10, items from "Examination ID number" on the top row (first row) to the row immediately before "Address of additional information of the first image on low-speed medium" are identical to those of examination information described in conjunction with Table 8. N in Table 10 represents the number of images involved in the examination.

The information search unit (DB-SRCH) 3d searches, as described previously,an information stored in the examination directory storage (DB-DIR) 3c according to a designated keyword in response to an instruction from the control (DB-CTRL) 3a, then writes the results of the search in system memory of the control 3a.

The image storage optical disk (DB-IOD) 3e is, for example, an optical disk.

The image storage magnetic disk (DB-IHD) 3f is, for example, a magnetic disk.

The image storage magnetic disk 3f stores almost the same data items as the image storage optical disk 3e.

Management information (addresses of data values, and amounts of data) indicating data items contained on the image storage magnetic disk 3f is stored on the image storage magnetic disk 3f in association with examination ID numbers.

The block memory (DB-BLKM) 3g is, for example, a semiconducting memory.

As described above, the diagnostic information creating means 104 of the present invention creates diagnostic information relative to examination images loaded into the workstation 4 as findings, inputs the created diagnostic information to the workstation 4, and allows the workstation 4 to create diagnostic information automatically.

The diagnostic information comparing means 105 compares the diagnostic information created as findings with the diagnostic information the workstation 4 creates.

The diagnostic information comparing means 105 mutually compares diagnostic information the workstation 4 creates, and allows the workstation 4 to create differences between diagnostic information in the form of time-sequential change data.

The diagnostic information output means 106 outputs a predetermined content to the workstation 4 when the diagnostic information created as findings is inconsistent with the diagnostic information the workstation creates.

The diagnostic information output means 106 allows the workstation 4 to determine relative positions for displaying interpretation image data serving as examination data according to predetermined relational information.

Figure 9:
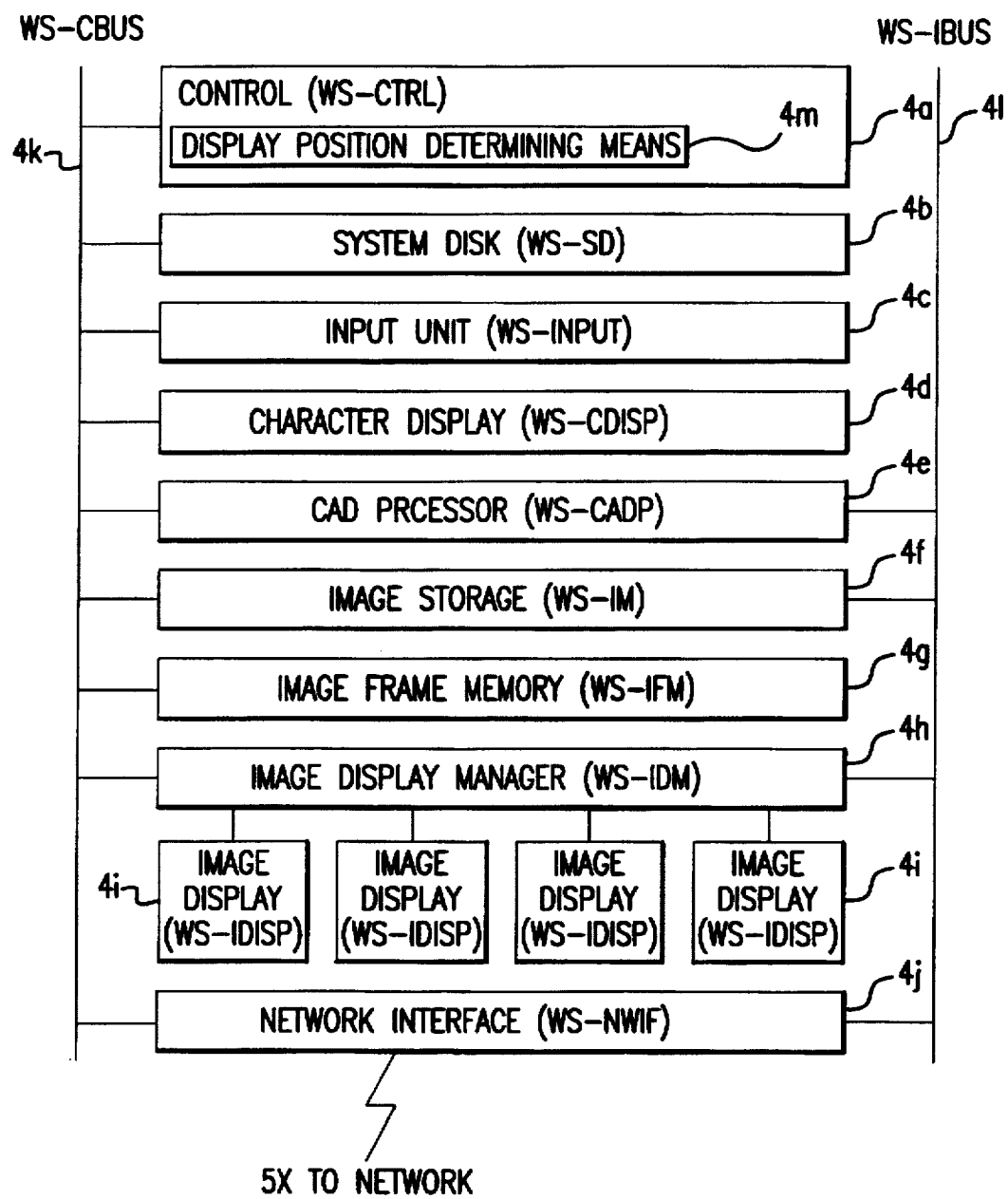
FIG. 9 is a configuration diagram of a workstation.

FIG. 9 is a detailed block diagram of the workstation (WS) 4.

The workstation (WS) 4 comprises a control (WS-CTRL) 4a capable of controlling the entire workstation 4, a system disk 4b for storing various data or programs, an input unit 4c for inputting diagnostic information created as findings, a character display 4d for displaying the diagnostic information or the results of comparing the diagnostic information, a CAD processor 4e serving as a computerizing means for creating diagnostic information relative to examination images, an image storage (WS-IM) 4f for storing examination image data temporarily, an image frame memory (WS-IFM) 4g or a semiconducting memory for storing data of multiple images temporarily, an image display manager 4h for controlling the display of image data, and an image display 4i for displaying image data.

The workstation 4 further comprises a network interface (WS-NWIF) 4j for communicating with other subsystems over the network 5, a control bus (WS-CBUS) 4k serving as a transmission path for various control information within the workstation 4, and an image bus (WS-IBUS) 41 serving as a transmission path for image data within the workstation 4.

The workstation 4 has a built-in clock (not shown) for referencing times and dates.

The control (WS-CTRL) 4a comprises a CPU and a system memory (semiconducting memory).

The system disk (WS-SD) 4b, as described above, stores various data together with programs for operating a work station (WS) 4. The information is read out when the power supply of the workstation 4 is turned on, then written in system memory of a control 3a.

The input unit (WS-INPUT) 4c allows operators to enter commands, interpretation reports, and other information, which is formed with a keyboard or a touch-sensitive screen.

The character display (WS-CDISP) 4d can display mainly characters including examination request information, examination histories, and interpretation reports, which is formed with a CRT display or a liquid crystal panel.

The CAD processor 4e has abnormality detection means capable of detecting predetermined lesions of, for example, pulmonary interstitial disease. The abnormality detection means applies to specific examination data to create diagnostic information relative to the examination data.

The abnormality detection means are algorithms for automatically detecting lesions such as those of a pulmonary interstitial disease by processing X-ray images and other examination data.

The CAD processor 4e includes multiple abnormality detection means; that is to say, in this embodiment:

(a) means for detecting shadows of pulmonary interstitial disease in a chest plain radiographic frontal image;

(b) means for detecting shadows of pulmonary nodules in a chest plain radiographic frontal image; and (c) means for detecting shadows of mammary fine calcification in a mammographic image.

The technology implemented in these abnormality detection means has been disclosed in Japanese Patent Laid-Open Nos. 2-185240, 2-152443, and 1-125675.

The CAD processor 4e contains abnormality detection means select information for associating abnormality detection means with items of examination data to which the abnormality detection means can apply.

Herein, "abnormality detection means select information" represents a correspondence table for associating data items of images (examined region, modality, examination procedure, and imaging direction) and types of detectable abnormalities detected in the images. Table 11 lists specific data values existent in the abnormality detection means select information.

TABLE 11

Example of abnormality detection means select information

| Examined region | Modality | Examination procedure | Imaging direction | Type of detectable abnormality |
|---|---|---|---|---|
| Chest | X-ray | Plain | P to A | Pulmonary interstitial disease |
| Chest | X-ray | Plain | P to A | Pulmonary nodules |
| Mamma | X-ray | Plain | Not specified | Fine calcification |

Data indicating types of detectable abnormalities (pulmonary interstitial disease, pulmonary nodules, and fine calcification) in Table 11 is used to inform the CAD processor 4e of abnormality detection means to be employed. The abnormality detection means select information can be rewritten.

Abnormality detection means select information should be stored in, for example, the system disk 4b.

The CAD processor 4e creates diagnostic information indicating the positions of abnormalities abnormality detection means detects and the degrees of the abnormalities.

The CAD processor 4e calculates the positions of abnormalities in association with image areas of interpretation image data or interpretation reference image data, then outputs the calculated positions of abnormalities as locations in an image in which the diagnostic information is displayed.

When positions of abnormalities are calculated, normal anatomical structures or image evaluation areas in an interpretation image or interpretation reference image should be used as references.

Recognizing normal anatomical structures and image evaluation areas is very important to determine areas for detecting abnormalities. Using the technology disclosed, for example, in Japanese Patent Laid-Open No. 1-125675, not only can the longitudinal center line of the mediastinum can be identified but also the infraclavicular margin, the supradiaphragmatic margin, and the costal position can be recognized in each of the right and left lungs.

Figure 10:
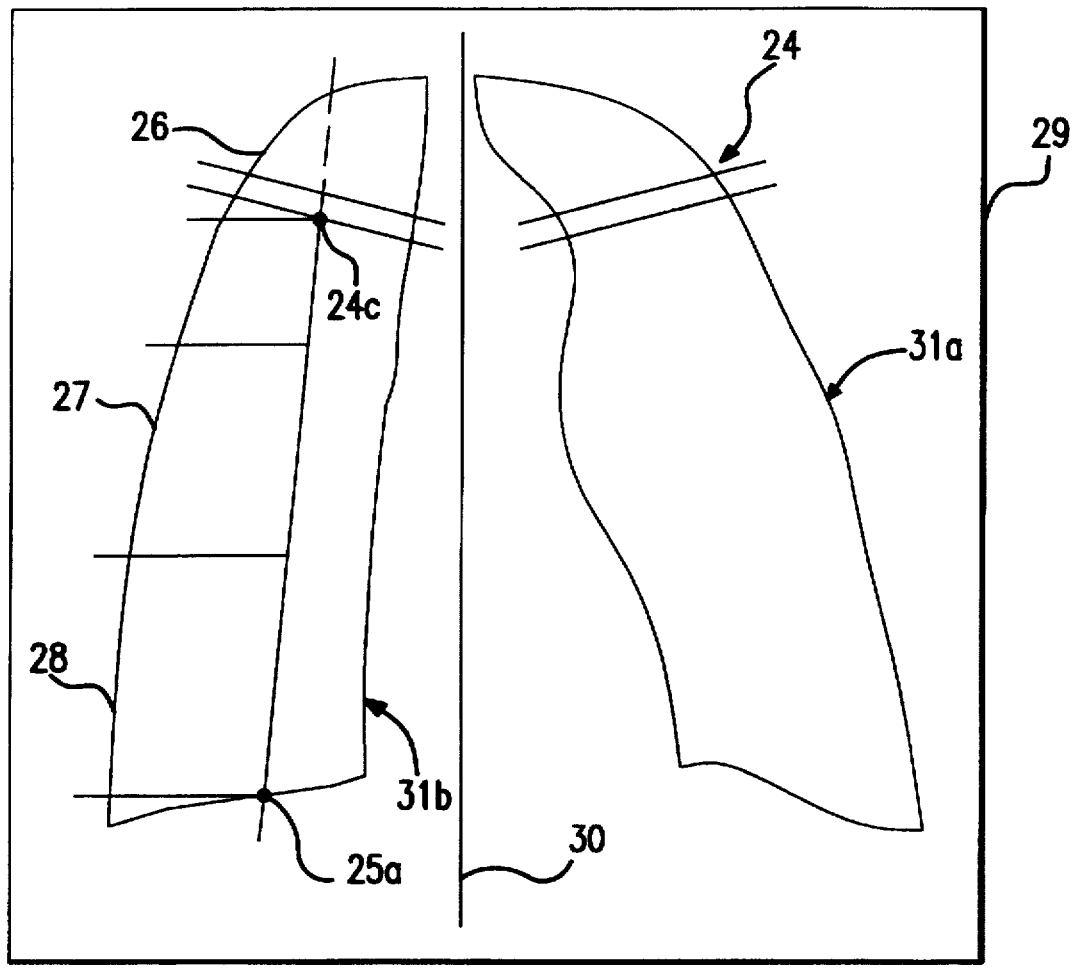
FIG. 10 shows lung field areas in a chest plain X-ray image.

According to the foregoing Japanese Patent Laid-Open No. 1-125675, the CAD processor 4e uses the coordinates of the infraclavicular margin and supradiaphragmatic margin in an image to calculate the areas of the superior, central, and inferior lung fields. The areas of the superior, central, and inferior lung fields should, in principle, be determined by assessing their positional relationships with the costal tips. However, the costal tips cannot be located precisely at present. Therefore, as shown in FIG. 10, the infraclavicular margin 24a and supradiaphragmatic margin 25a are located to calculate the areas of the superior, central, and inferior lung fields. 24 denotes the clavicle.

Specifically, the trisecting lines of a straight line from the superior margin of the lung field to the inferior margin of the lung field are recognized as the borders between the superior lung field 26 and central lung field 27, and the central lung field 27 and inferior lung field. The infraclavicular margin 24a lies almost on the center of the superior lung field 26. Positions are determined according to the following procedure:

(a) The position (X coordinate) of the longitudinal center line of the mediastinum 30 is determined in an X-ray film 29.

(b) The positions of the infraclavicular margin 24a and supradiaphragmatic margin 25a are determined for each of the left and right lungs 31a and 31b.

(c) The positions (Y coordinates) of the infraclavicular margins 24a in the left and right lungs 31a and 31b are averaged and recognized as the position of the infraclavicular margin 24a of the whole lung.

(d) The positions (Y coordinates) of the supradiaphragmatic margins 25a in the left and right lungs 31a and 31b are averaged and recognized as the position of the supradiaphragmatic margin 25a in the whole lung. (e) On the straight line connecting between the positions of the infraclavicular margin 24a and the supradiaphragmatic margin 25a, a one-sixth position on the side of the infraclavicular margin 24a is recognized as the border between the superior lung field 26 and central lung field 27.

(f) On the straight line connecting between the positions of the infraclavicular margin 24a and supradiaphragmatic margin 25a, a three-sixths (half) position on the side of the infraclavicular margin 24a is recognized as the border between the central lung field 27 and inferior lung field 28.

The diagnostic information output means 106 uses an image display manager 4h to superimpose the created diagnostic information on an examination image so that the diagnostic information will be displayed at the aforesaid positions of abnormalities.

As described above, the diagnostic information comparing means 105 compares diagnostic information workstation 4 creates mutually, and uses the workstation 4 to create differences between diagnostic information in the form of time-sequential change data.

Specifically, the diagnostic information comparing means 105 subtracts degrees existent in interpretation reference image data from degrees existent in interpretation image data, then makes the differences into time-sequential data.

Time-sequential data should include predetermined indices indicating progresses of abnormalities or lesions of interest; such as, "Onset," "In progress," "Recovered," and "Fade-out."

The diagnostic information output means 106 uses the image display manager 4h to superimpose the contents of time-sequential change data on an associated examination image in a mutually-discernible manner.

For discernible superimposition of the contents of time-sequential change information, display colors should be varied according to the relational information between time-sequential abnormality changes and display colors.

"Relational information between time-sequential abnormality changes and display colors" represents colors in which time-sequential abnormality changes are superimposed on an image. Table 12 shows an example.

TABLE 12

Example of relational information between time-sequential abnormality changes and display colors

| Time-sequential abnormality change | Display color |
| --- | --- |
| Onset | Red |
| In progress | Yellow |
| Unchanged | Green |
| Recovered | Light blue |
| Fade-out | Blue |

The meanings of time-sequential changes in Table 12 will be described later. The relational information between time-sequential abnormality changes and display colors can also be rewritten.

The diagnostic information output means 106, as described previously, uses the image display manager 4h to output a predetermined content when the diagnostic information created as findings is inconsistent with the diagnostic information the CAD processor 4e creates.

The diagnostic information output means 106 has display position determining means 4m for determining a relational information, for example imaging directions of chest plain X-ray images and relative display positions, and storing the relational information in, for example, the system disk 4b. Based on the relational information, a relative display position of a chest plain X-ray image or the image display 4i on which the chest plain X-ray image is displayed is determined automatically.

The display position determining means 4m should be provided in the control(WS-CTRL) 4a,but may be provided in the workstaion 4 , the data acquisition apparatus 2,or the database 3.

"Relational information between imaging directions of chest plain X-ray images and relative display positions" represents information for automatically determining image display positions. Table 13 shows an example.

TABLE 13

Example of relational information between imaging directions of chest plain X-ray images and relative display positions

| Imaging direction | Relative image display position |
| --- | --- |
| P to A | C |
| L to R | L |
| R to L | R |

The meanings of items in Table 13 are as follows:

"P to A" indicates that an X-ray is projected from a patient' posterior. This projection provides a frontal image.

"L to R" indicates that an X-ray is projected from a patient's left lateral. This projection provides a right lateral image.

"R to L" indicates that an X-ray is projected from a patient's right lateral. This projection provides a left lateral image.

"C" indicates that an image is displayed on the center.

"L" indicates that an image is displayed on the left of a P-to-A image (frontal image).

"R" indicates that an image is displayed on the right of a P- to-A image (frontal image).

Needless to say, the information in Table 13 can be rewritten.

If the image display 4i can't display the all images simultaneously, the image display 4i may display the images according to a predetermined priority.

The predetermined priority data can be added to the relational information between imaging directions and relative display positions.

For example, it the predetermined priority define "P to A,L to R,R to L", and if two image displays 4i are provided, each image display 4i display the image of P to A, and L to R.

The system disk 4b should further contain an interpreting doctor information table.

"The interpreting doctor information table" represents a correspondence table between interpreting doctor ID numbers and interpreting doctor names. Table 14 shows an example.

TABLE 14

Example of an interpreting doctor information table

| Interpreting doctor ID number | Interpreting doctor name |
| --- | --- |
| 1856 | S. Kato |
| 2965 | N. Yamaguchi |
| 3476 | T. Takeda |
| : | : |
| : | : |

The interpreting doctor information table can be rewritten.

When any of the aforesaid rewritable data values must be modified, a table containing an intended data value is displayed on a character display (WS-CDISP) 4d, a new value is entered at an input unit (WS-INPUT) 4c, and then updated data is overwritten on the data before updating.

Figure 11:
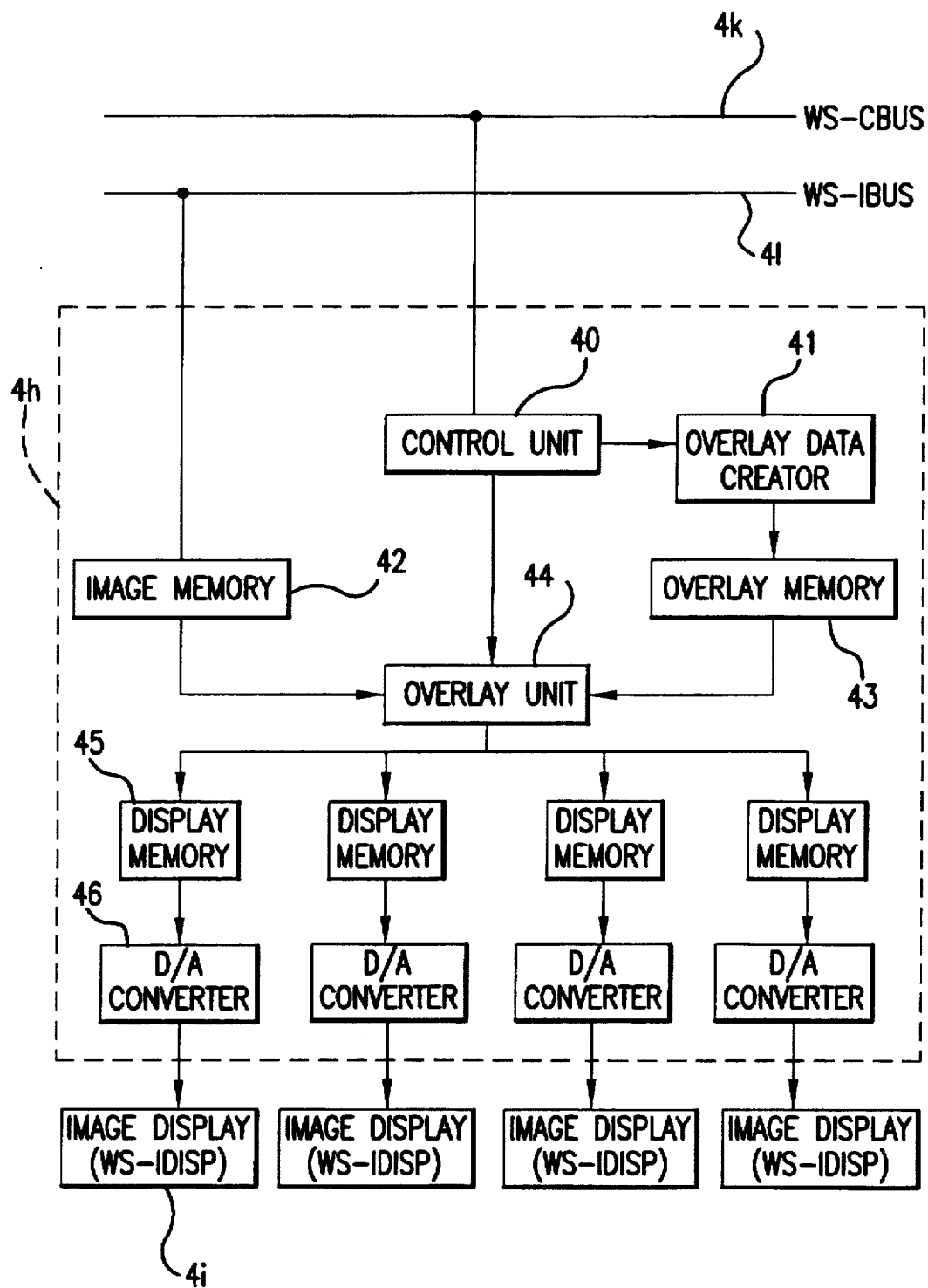
FIG. 11 is a configuration diagram of an image display manager of a workstation.

FIG. 11 is a detailed block diagram of the image display manager 4h.

As shown in FIG. 11, the image display manager 4h comprises:

a control unit 40 for controlling the entire image display manager 4h, and receiving information indicating data items displayed, designation information indicating the device number of an image display for displaying data, and overlay display information or information concerning overlay graphics;

an overlay creator 41 for creating overlay data according to overlay display information in response to an instruction from the control unit;

an image memory 42 for receiving and storing image data;

an overlay memory 43 for storing the overlay data in response to an instruction from the control unit;

an overlay unit 44 for superimposing the overlay data on image data to create display data in response to an instruction from the control unit;

display memories 45 each storing the synthetic display data in association with an image display of a designated device number; and D/A converters 46 each converting the stored display data from the digital to analog form.

Among information the control unit 40 receives, information indicating data items to be displayed may specify image data only, overlay data only, or image and overlay data.

Overlay display information specifies a type of graphic, a size of a graphic, coordinates, a display color, and flicker control information for each graphic.

The overlay data creator 41 can create overlay data in color and has a means for flickering designated data of overlay display information.

An image memory 42 has a memory for storing one image (2048 by 2048 matrix size).

Figure 12:
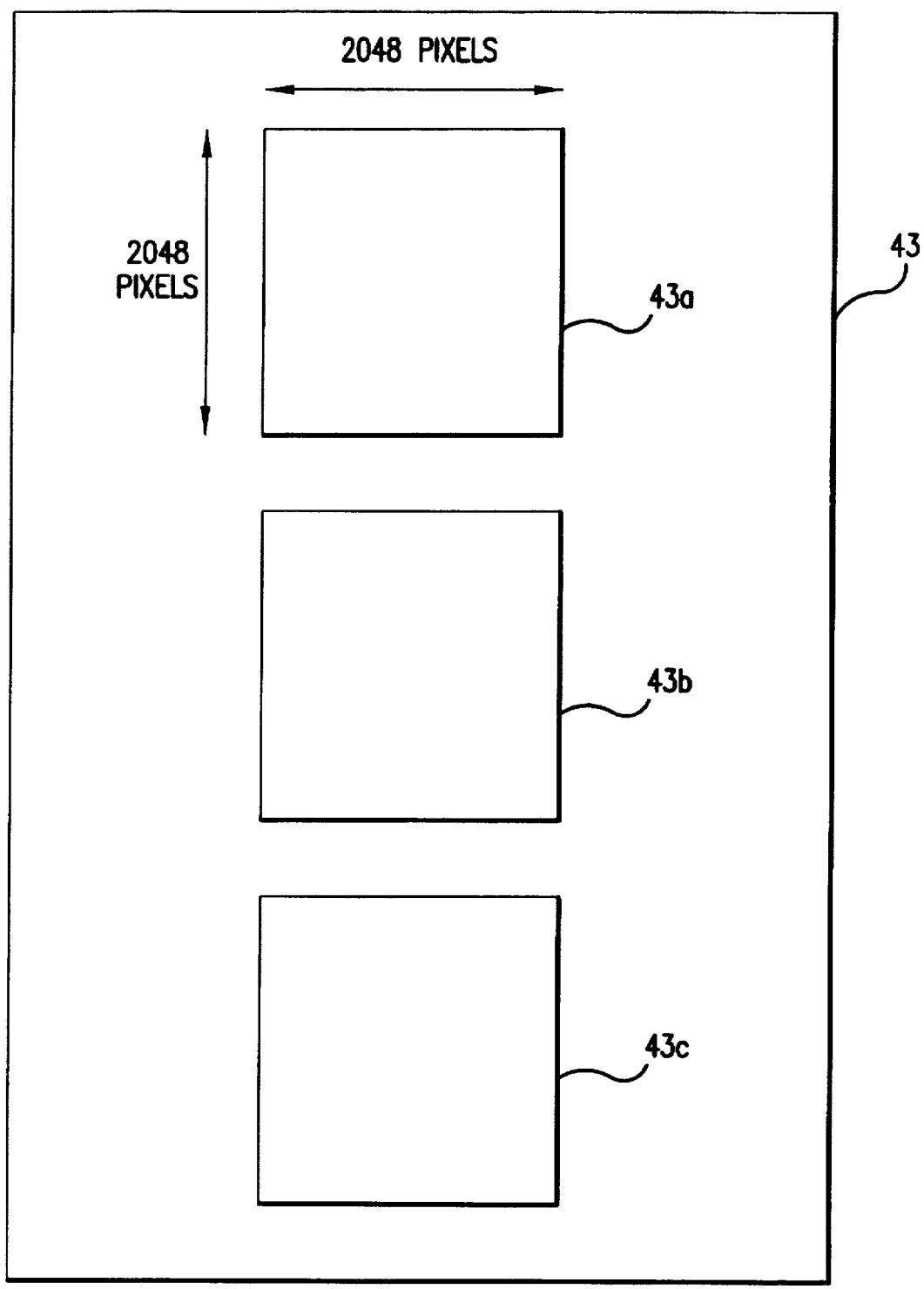
FIG. 12 is a configuration diagram of an overlay memory.

An overlay memory 43 is made up of overlay memories 43a, 43b, and 43c storing red, green, and blue data in screens, as shown in FIG. 12, so that it can store colored overlay data.

Each of the color overlay memories 43a, 43b, and 43c supports a matrix size of 2048 by 2048 pixels. Herein, one pixel is one bit long.

Table 15 shows the relationships between display colors and pixel bit values.

TABLE 15

Relationships between display colors and pixel bit values specified in overlay memories

| Display color | Bit value in red overlay memory | Bit value in green overlay memory | Bit value in blue overlay memory |
| --- | --- | --- | --- |
| Black | 0 | 0 | 0 |
| Red | 1 | 0 | 0 |
| Green | 0 | 1 | 0 |
| Blue | 0 | 0 | 1 |
| Yellow | 1 | 1 | 0 |
| Purple | 1 | 0 | 1 |
| Light blue | 0 | 1 | 1 |
| White | 1 | 1 | 1 |

For example, as shown in the second row of Table 15, when the pixel value (or pixel bit value) at pixel coordinates (X, Y) in red overlay memory is 1, if the pixel values at the same coordinates in green and blue overlay memories, 0s, the pixel at the coordinates is displayed in red. On the other hand, a display color, black, means that no color appears. Therefore, when overlay data is superimposed on an image, only the image is displayed.

As shown in FIG. 11, four display memories 45 each having a capacity of one image (in a matrix size of 2048 by 2048 pixels) are incorporated in association with image displays 4i.

The display memories 45 are associated with the image displays 4i.

The number of D/A converters 46 agrees with the number of image displays 4i.

Thus, when overlay data is to be superimposed on image data, the image display manager 4h, first, uses the control unit 40 to receive information specifying data items to be displayed or "image data and overlay data," an image display device number of an image display for displaying data, and overlay display information from the control 4a of the workstation 4, and places received image data in the image memory 42. Then, in response to an instruction from the control unit 40, the overlay data creator 41 creates overlay data according to overlay display information specifying a designated graphic, designated coordinates, and designated color data. In response to an instruction from the control unit 40, the image data and overlay data are read out. The overlay unit 44 synthesizes the read image data and overlay data. The synthetic data is written in the display memory 45 associated with the image display of the designated device number. The D/A converter 46 converts the data into analog data. Then, the converted data is displayed on the image display 4i.

When flickering control information specifies "flickering" for a graphic at certain coordinates, the overlay data creator 41 writes and deletes the graphic in and from the overlay memory 43 at regular intervals of 0.5 to 1 second. Thus, the graphic flickers on the display.

On the other hand, when an image alone is to be displayed, the image display manager 4h receives information specifying "image data only" as data items to be displayed and a device number of a display for displaying data, but neither reads out overlay data nor superimposes overlay data on image data.

The meaning of a "size of a graphic" existent in overlay display information varies depending on a type of graphic. For example, if "arrow" is specified as a type of graphic, the size of a graphic represents the length of an arrow.

The image storage (WS-IM) 4f can temporarily store:

(a) interpretation reference priority information;

(b) examination request information;

(c) examination histories;

(d) interpretation reports;

(e) additional information;

(f) image data;

(g) overlay display information;

(h) abnormality data table; and (i) time-sequential abnormality change data table, which is formed with, for example, a magnetic disk.

An image display (WS-IDISP) 4i is formed with a color CRT display capable of displaying images in a maximum matrix size of 2048 by 2048 pixels. In this embodiment, four image displays are installed.

Next, a sequence of system operations for interpretation using a PACS having the aforesaid configuration will be described. Interpreting chest X-ray images will be discussed as an example. System operations proceed, for example, as follows:

1. Receiving examination request information
2. Acquiring and storing images
3. Loading images to be interpreted
4. Executing CAD processing and creating diagnostic information
5. Interpreting images and entering an interpretation report by an interpreting doctor
6. Comparing diagnostic information and calling an interpreting doctor's attention
7. Referencing the results of CAD processing by the interpreting doctor
8. Completing and storing the interpretation report In chest plain X-ray radiography, two or more radiographs are taken during an examination. For example, the following three images are produced:

(a) one frontal image, (b) one right lateral image, and (c) one left lateral image.

Figure 13A:
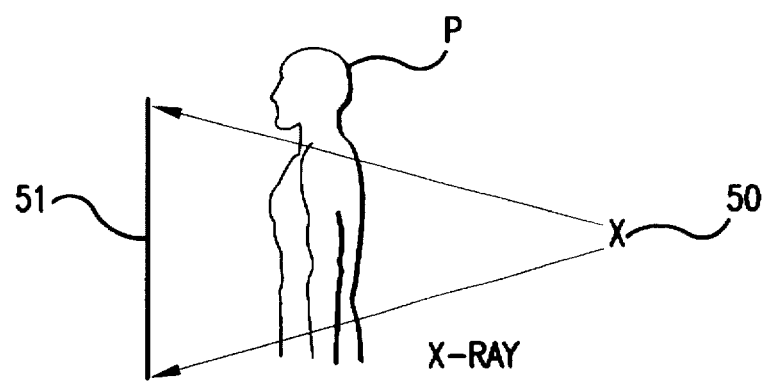
FIG. 13 shows the positional relationships among an Xray source, a patient, and an X-ray film for providing frontal, and right and left lateral images.
Figure 13B:
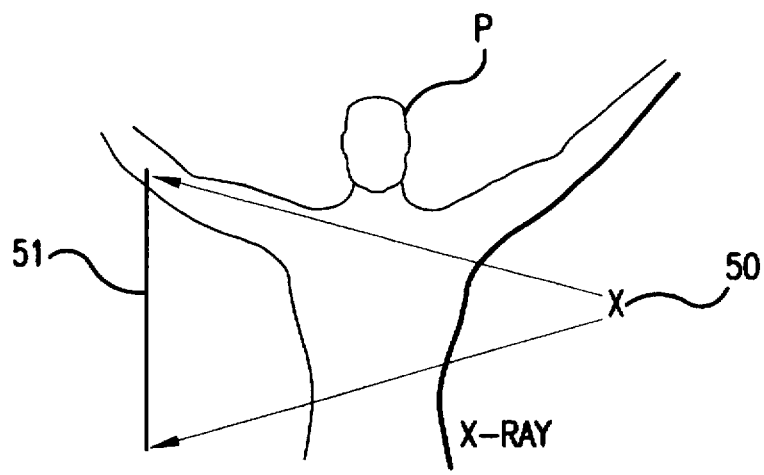
Figure 13C:
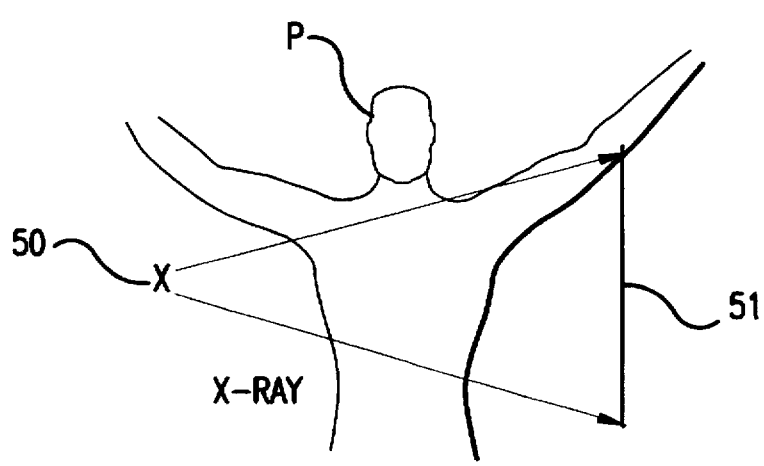

Herein, as shown in FIGS. 13(A), (B), and (C), a frontal image shall be produced by projecting an X-ray from the posterior of a patient P onto an X-ray film 51 placed in front of the patient. A right lateral image shall be produced by projecting an X-ray from the left lateral of the patient P onto an X-ray film 51 placed on the right of the patient P. A left lateral image shall be produced by projecting an X-ray from the right lateral of the patient P onto an X-ray film placed on the left of the patient P. In FIGS. 13(A), (B), and (C), 50 denotes an X-ray generator.

Figure 14:
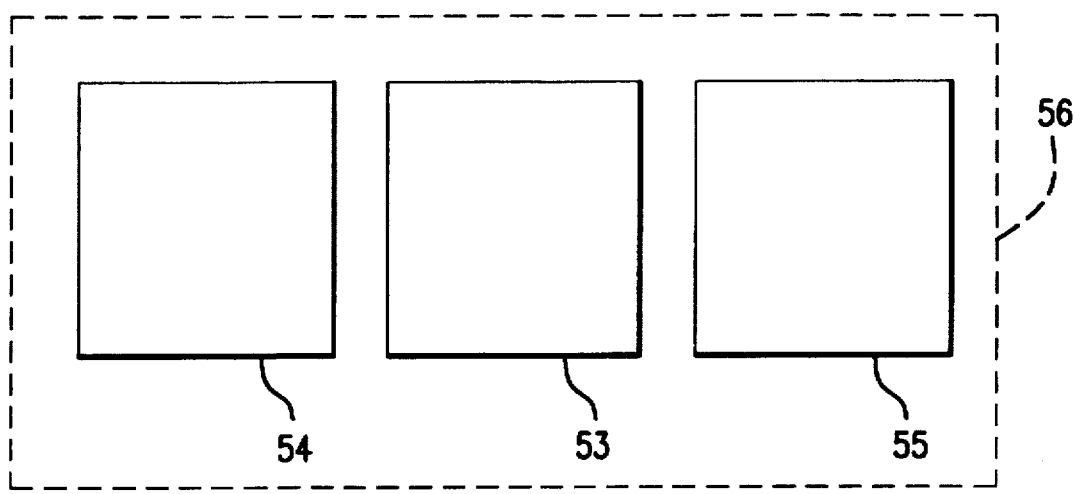
FIG. 14 shows the viewing arrangement of radiographs taken in different imaging directions.

When a doctor interpreting images arranges films on a film viewer to observe the images, he/she usually arranges them as shown in FIG. 14. That is to say:

(1) A doctor interpreting images arranges the films as if he/she were looking at an X-ray source from the film position during radiography.

(2) When it comes to the above three kinds of images, the frontal image 53 is placed on the center, the right lateral image 54, on the left of the frontal image 53, and the left lateral image 55, on the right of the frontal image.

In FIG. 14, 56 denotes a film viewer.

Each of the aforesaid sequence of system operations will be described in detail.

1. Receiving an Examination Request Sheet (1) Receiving examination request information from the examination order system 7

1.1.1) Examination request information the examination order system 7 has created reaches the network interface (SM-NWIF) 1h of the system manager 1.

1.1.2) The control (SM-NWIF) 1a fetches examination request information from the network interface 1h and transfers the information to the system memory in the control 1a.

(2) Issuing an examination ID number and storing examination request information 1.2.1) The control (SM-CTRL) 1a instructs the examination ID number issuing unit (SM-EIDI) 1c to issue an examination ID number.

1.2.2) The examination ID number issuing unit 1c increments the current examination ID number by 1 and returns a new number to the control 1a. The examination ID number is inherent to this examination.

1.2.3) The control 1a combines the issued examination ID number and the examination request information, then writes the combined data in the examination request information storage (SM-EOIM) 1d. Table 16 lists an example of combined data of a written examination ID number and examination request information in a listing form.

TABLE 16

Example of data values existent in examination request information combined with an issued examination ID number under the system manager

| Data item | Data value |
| --- | --- |
| Examination ID number | 103541 |
| Patient ID number | 870802 |
| Patient name | T. Suzuki |
| Date of birth | August 6, 1955 |
| Sex | Male |
| Modality | X-ray |
| Examined region | Chest |
| Examination procedure | Plain radiography |
| Examination requesting department | Department of Internal Medicine |
| Examination requesting doctor | M. Tanaka |
| Date of examination request | January 22, 1990 |
| Requested date of examination | January 22, 1990 |
| Requested time of examination | 2:00 p.m. |
| Purpose of examination | Prognosis |
| Patient clinical information | Dyspnea, cough, expectoration |
| Disclosed disease | Interstitial pneumonia |
| : | : |
| : | : |

A terminal (not shown in FIG. 2) to be connected on the network 5 in FIG. 2 is installed in an examination room. A radiologic technologist can use the terminal to display examination request information (including an examination ID number) listed in Table 16.

2. Acquiring and Storing Images (1) Acquiring digital images 2.1.1) An operator places exposed and developed X-ray films for one examination in the film density reader (FDG-FR) 2c of the film digitizer 2, then enters a digitization command at the input unit (FDG-INPUT) 2d.

In this embodiment, two chest plain radiographs visualizing frontal and left lateral images shall be placed.

2.1.2) The film digitizer 2a instructs the film density reader 2c to digitize film densities.

2.1.3) The film density reader 2c reads the densities of the films placed, then digitizes the images in films to produce digital images each having a size of 2048 pixels by 2048 pixels by 10 bits. The digitized images are written in the image data storage (FDG-IM) 2g.

Digitizing film densities and writing data in the image data storage 2g are performed in films. These two operations are repeated for the number of films placed. In this case, the repetition frequency is two.

2.1.4) The control 2a of the film digitizer 2 automatically generates part of additional information for each of two images, then writes the data in an examination information/additional information storage (FDG-EIIM) 2f. Table 17 lists part of data items included in additional information for an image of the second film and the automatically-gene rated data values.

TABLE 17

Example of data items included in additional information and their data values automatically generated by the film digitizer in this embodiment

| Data item | Data value |
| --- | --- |
| Examination ID number | |
| Image number (image number within the examination) | 2 |
| Pixel size 1 (lateral length of pixels) | 0.016 cm |
| Pixel size 2 (longitudinal length of pixels) | 0.016 cm |
| Matrix size 1 (number of pixels in lateral direction) | 2048 |
| Matrix size 2 (number of pixels in longitudinal direction) | 2048 |
| Pixel bit length | 10 |
| Amount of data | 5 M bytes |
| Imaging direction | |
| : | : |
| : | : |

For data items for which no data values are specified in Table 17, the values cannot be determined automatically.

(2) Entering examination information and additional information 2.2.1) The control (FDG-CTRL) 2a of the film digitizer 2 displays necessary items of examination information on a screen of the display (FDG-DISP) 2e of the film digitizer 2.

2.2.2) Two images digitized with an instruction from the control 2a of the film digitizer 2 are read out from an image data storage (FDG-IM) 2g, transmitted to and minified by the image minification unit (FDG-IMIN) 2h, then displayed on the display 2e.

2.2.3) The control 2a of the film digitizer 2 displays necessary items of additional information on a screen of the display 2 in association with images. FIG. 15 shows an example of a display screen at this stage. 58 denotes a display screen of the display 2e.

Many examination data is digitized within the day of examination. Therefore, a date is retrieved from a built-in clock of the film digitizer 2, and thus a date of examination is displayed automatically. Since two films have been digitized, 2 is specified as the number of images.

2.2.4) An operator first enters an examination ID number at the input unit (FDG-INPUT) 2d. The control 2a writes the entered examination ID number in the examination information/additional information storage (FDG-EIIM) 2f, then displays it on the display 2e.

2.2.5) Next, the control 2a of the film digitizer 2 communicates with the system manager (SM) 1 via the network interface (FDG-NWIF) 2i, sends the entered examination ID number to the system manager 1, then requests the system manager 1 to transfer examination request information.

2.2.6) On receipt of a request from the film digitizer 2, the system manager 1 passes the received examination ID number to the information search unit (SM-SRCH) 1g, and instructs the information search unit 1g to search for examination request information.

2.2.7) The information search unit 1g of the system manager 1 accesses the examination request information storage (SM-EOIM) 1d, searches for examination request information having the same examination ID number as the passed one, reads out the examination request information, then writes the information in system memory of the control 1a of the system manager 1.

2.2.8) The control 1a of the system manager 1 transfers the read examination request information to the network interface 1h, then instructs the network interface 1h to transfer the data to the film digitizer 2. Then, the network interface 1h sends the examination request information to the film digitizer 2.

2.2.9) When the network interface 2i of the film digitizer 2 receives the examination request information from the system manager 1, the control 2a of the film digitizer 2 reads out the transferred examination request information from the network interface 2i, then writes it in system memory of the control 2a.

2.2.10) The control 2a of the film digitizer 2 displays values of the examination request information, which have been written in the system memory immediately before, concerning items to be displayed; such as, a patient name, a patient ID number, a date of birth, a sex, an examination modality, an examined region, an examination procedure, an examination requesting department, and an examination requesting doctor, at predetermined positions on the display 2e.

2.2.11) The operator monitors the patient name and examination information displayed to see if the values are correct. If the operator finds incorrect data, he/she enters a correct value at the input unit 2d. The control 2a rewrites the value of the data item stored in the examination information/additional information storage 2f, then displays the corrected data at the predetermined position on the display 2e.

2.2.12) The operator enters additional information. In this case, the operator enters the imaging directions of the two images at the input unit 2d. The control 2a writes the entered imaging direction data in the examination information/additional information storage 2f, then displays the values at the predetermined positions on the display 2e.

2.2.13) When completing data entry, the operator enters an input termination command at the input unit 2d of the film digitizer.

FIG. 16 shows information displayed on a screen of the display 2e at this stage. 58 denotes a display screen of the display 2e. The meanings of P to A and R to L are as described in conjunction with Table 13. These imaging directions provide frontal and left lateral images.

Tables 18 and 19 lists the data values of examination information and of additional information written in the examination information/additional information storage 2f at this stage.

TABLE 18

Example of data values of examination information written in the examination information/additional information storage when an operator completes entering necessary data after the film digitizer has digitized film densities

| Data item | Data value |
| --- | --- |
| Examination ID number | 103541 |
| Patient ID number | 870802 |
| Patient name | T. Suzuki |
| Date of birth | August 6, 1952 |
| Sex | Male |
| Modality | X-ray |
| Examined region | Chest |
| Examination procedure | Plain |
| Examination requesting department | Department of Internal Medicine |
| Examination requesting doctor | M. Tanaka |
| Date of examination | January 22, 1990 |
| Number of images | 2 |
| : | : |

TABLE 19

Example of data values of additional information written in the examinaion information/additional information storage when an operator completes entering necessary data after the film digitizer has digitized fil densities

| Data item | Data value |
| --- | --- |
| For the first image | |
| Examination ID number | 103541 |
| Image number (image number within the examination) | 1 |
| Pixel size 1 (lateral length of pixels) | 0.016 cm |
| Pixel size 2 (longitudinal length of pixels) | 0.016 cm |
| Matrix size 1 (number of pixels in the lateral direction) | 2048 |
| Matrix size 2 (number of pixels in the longitudinal direction) | 2048 |
| Pixel bit length | 10 |
| Amount of data | 5 M bytes |
| Imaging direction | P to A |
| : | : |
| For the second image | |
| Examination ID number | 103541 |
| Image number (image number within the examination) | 2 |
| Pixel size 1 (lateral length of pixels) | 0.016 cm |
| Pixel size 2 (longitudinal length of pixels) | 0.016 cm |
| Matrix size 1 (number of pixels in the lateral direction) | 2048 |
| Matrix size 2 (number of pixels in the longitudinal direction) | 2048 |
| Pixel bit length | 10 |
| Amount of data | 5 M bytes |
| Imaging direction | R to L |
| : | : |

(3) Transferring data to a database 2.3.1) When an input termination command is entered, the control (FDG-CTRL) 2a reads out the examination information (including patient information and an examination ID number) of an examination concerned and the additional information of images from the examination information/ additional information storage (FDG-EIIM) 2f, and image data from the image data storage (FDG-IM) 2g, and then transfers the read data to the network interface (FDG-NWIF) 2i. That is to say, the image data is combined with the data values of examination information and of additional information listed in Tables 18 and 19, then sent to the network interface 2i. The control 2a instructs the network interface 2i to transmit the data to the database 3.

2.3.2) The network interface 2i transfers the received data to the database 3.

(4) Registering and storing examination information, additional information, and image data 2.4.1) When data sent from the film digitizer 2 reaches the network interface (DB-NWIF) 3h of the database 3, the control (DB-CTRL) 3a of the database 3 reads out the transferred data from the network interface 3h, then writes the data in block memory (DB-BLKM) 3g.

2.4.2) The control 3a fetches the image data and additional information written in the block memory 3g into the image storage magnetic disk (DB-IHD) 3f.

2.4.3) The control 3a fetches the image data and additional information written in the block memory 3g into the image storage optical disk (DB-IOD) 3f, then calculates the addresses of the additional information and image data for each image (two images in this example). Then, the control 3a calculates the amount of data of additional information for each image.

2.4.4) The control 3a writes the directory information of the examination in an examination directory inside the examination directory storage (DB-DIR) 3c. The data items of information contained in the examination directory have been presented in conjunction with Table 10. The values resulting from this operation are provided as the addresses of additional information and image data, and the amounts of data of additional information and image data for each image. Other data values are included in the examination information and additional information. Therefore, required data can be copied from the examination information and additional information.

2.4.5) The control 3a reads out the examination information of the examination from the block memory 3g, then transfers the information to the system manager 1 via the network interface 3h.

(5) Appending an examination history 2.5.1) When examination information sent from the database 3 reaches the network interface (SM-NWIF) 1h of the system manager (SM) 1, the control (SM-CTRL) 1a of the system manager 1 reads out the examination information from the network interface 1h, then writes it in system memory of the control 1a.

2.5.2) The control 1a fetches a patient ID number from the examination information placed in system memory, sends the patient ID number to the information search unit (SM-SRCH) 1g, then instructs the information search unit 1g to search for an examination history of a patient having the patient ID number.

2.5.3) The information search unit 1g accesses and searches the examination history storage (SM-EHM) 1e, reads out the examination history of the patient having the patient ID number sent from the control 1a, then writes the examination history in system memory of the control 1a.

2.5.4) The control 1a fetches only data values required as examination history data from the examination information transferred from the database 3, then appends the data values to the examination history data placed in system memory.

The control 1a writes the examination history with new data appended in the examination history storage 1e. Thus, new examination information has been appended to the patient's examination history.

Table 20 lists the data values of the patient's examination history (with new data appended) in this embodiment.

TABLE 20

Example of data values of a patient's examinaion history

| Data item | Data value |
|---|---|
| Patient information | |
| Patient ID number | 870802 |
| Patient name | T. Suzuki |
| Date of birth | August 6, 1952 |
| Sex | Male |
| Information of the first examination | |
| Examination ID number | 60563 |
| Modality | CT |
| Examined region | Brain |
| Examination procedure | Contrast medium administered |
| Examination requesting department | Department of Neurosurgery |
| Examination requesting doctor | S. Kimura |
| Date of examination | April 15, 1989 |
| Number of images | 20 |
| Information of the second examination | |
| Examination ID number | 100902 |
| Modality | X-ray |
| Examined region | Chest |
| Examination procedure | Plain |
| Examination requesting department | Department of Internal Medicine |
| Examination requesting doctor | M. Tanaka |
| Date of examination | January 12, 1990 |
| Number of images | 2 |

3. Loading Images to be Interpreted (1) Instructing a database to load previous images 3.1.1) The control (SM-CTRL) 1a of the system manager 1 checks patient's examination history data in system memory of the control 1 for the examined region, modality, and date of exasminations in units of examinations, then gives interpretation priorities to the examinations. Then, the interpretation priorities are stored as interpretation reference priority information in association with the examination ID numbers of the examinations. Table 21 lists the data value of interpretation reference priority information. In Table 21, an examination having an interpretation reference priority 0 is an interpretation examination or an examination whose relevant images are about to be interpreted.

TABLE 21

Example of data values of interpretation reference priority information

| Examination ID number | Interpretation reference priority |
|---|---|
| 103541 | 0 |
| 100902 | 1 |
| 102287 | 2 |
| 60563 | 3 |

3.1.2) The control 1a of the system manager 1 reads out the interpretation reference priority information data from system memory, transfers the data into the network interface (SM-NWIF) 1h, and instructs the network interface 1h to send the data to the database (DB) 3. The network interface 1h transmits the interpretation reference priority information data to the database 3.

(2) Reading out previous images from a low-speed medium to a high-speed medium inside the database 3.2.1) When the interpretation reference priority information data reaches the network interface (DB-NWIF) 3h of the database (DB) 3, the control (DB-CTRL) 3a of the database 3 reads out the interpretation reference priority information data from the network interface 3h, then writes the data in system memory of the control 3a.

3.2.2) The control 3a of the database 3 provides the information search unit (DB-SRCH) 3d with examination ID numbers existent in the interpretation reference priority information data, then instructs the information search unit 3d to search for and read out the examination directory information of the examinations.

3.2.3) The information search unit 3d accesses the examination directory storage 3c to search the examination directories, reads out the examination directory data of examinations having examination ID numbers 103541, 100902, 102287, and 60563, then writes the read data in system memory of the control 3a.

3.2.4) The control 3a of the database 3 confirms that the image data and additional information data of the examination (uninterpreted) having an examination ID number 103541 have been written on the image storage magnetic disk (DB-IHD) 3f. If the data is not stored, all the image data and additional information data involved in the examination is read out from an image storage optical disk (DB-IOD) 3e, then writes the data on the image storage magnetic disk 3f.

3.2.5) Next, the control 3a of the database 3 reads out all the image data and additional information data of the examinations having examination ID numbers 100902, 102287, and 60563 from the image storage optical disk 3e, then writes the read data on the image storage magnetic disk 3f. Reading previous examination images into the image storage magnetic disk 3f is executed in order of priorities specified in the interpretation reference priority information data. Therefore, if the image storage magnetic disk 3f becomes full and cannot contain any more data before reading is complete, images involved in examinations given higher priorities remain written on the image storage magnetic disk 3f. This means that previous examination images having higher possibilities of being referenced during interpretation have been written on the image storage magnetic disk 3f.

(3) Instructing the workstation to load images When the system manager (SM) 1 instructs the database 3 to load previous images, patient's (T. Suzuki) examination history (with new data appended) data and interpretation reference priority information data reside in system memory of the system manager 1.

3.3.1) The control 1a of the system manager 1 selects the examination ID number of an interpretation examination (which is given a top priority 0, or an examination having an examination ID number 103541 in this example) from the patient's interpretation reference priority information data written in system memory of the control 1a, sends the examination ID number to the information search unit (SM-SRCH) 1g, then instructs the information search unit 1g to search for and read out examination request information of an examination having the examination ID number.

3.3.2) The information search unit 1g accesses the examination request information storage (SM-EOIM) 1d and searches the storage as instructed. Then, the information search unit 1g reads out the examination request information data of an examination having the examination ID number sent from the control 1a, then writes the read data in system memory of the control 1a.

3.3.3) The control 1a of the system manager 1 fetches the examination ID numbers of all (four in this example) examinations from the patient's interpretation reference priority information data written in system memory of the control 1a and sends the examination ID numbers to the information search unit 1g. Then, the control 1a instructs the information search unit 1g to search for and read out the interpretation reports relevant to examinations having the examination ID numbers.

3.3.4) The information search unit 1g accesses the interpretation report storage (SM-IDRM) 1f and searches the storage as instructed. Then, the information search unit 1g reads out the interpretation reports relevant to the examinations having the examination ID numbers the control 1g has provided, then writes the read data in system memory of the control 1a.

3.3.5) The control 1a of the system manager references workstation vs. interpretation examination modality information and selects an ID of a workstation 4 at which an operator interprets images acquired in a chest plain X-ray examination having an examination ID number 103541.

The data existent in workstation vs. interpretation examination modality information has already been described in conjunction with Table 4.

The workstation vs. interpretation examination modality information reveals that images acquired in a chest plain X-ray examination (examination ID number 103541) or a patient's (T. Suzuki) interpretation examination is supposed to be interpreted at a workstation having an ID WS-1 or WS-2. In this case, WS-1 shall be selected.

The images acquired in the next X-ray examination are interpreted using WS-2 so that the loads to the workstations 4 will be equalized.

3.3.6) The control 1g of the system manager 1 transfers the examination request information (specified with an examination ID number 103541 in this case), patient's (T. Suzuki) examination history data, interpretation reference priority information data, and interpretation reports relevant to previous examinations (three examinations in this case) written in system memory of the control 1g to the network interface 1h, then instructs the network interface 1h to send the data to the WS-1. The network interface 1h sends the received data to the WS-1.

(4) Loading images into the workstation 3.4.1) When data (examination request information, an examination history, interpretation reference priority information, and interpretation reports) sent from the system manager 1 reaches the network interface (WS-NWIF) 4j of the workstation WS-1, the control (WS-CTRL) 4a of the workstation WS-1 reads out the received data from the network interface 4j, then writes the data in system memory of the control 4a.

3.4.2) The control 4a of the workstation WS-1 writes the examination request information, examination history, interpretation reference priority information, and interpretation reports in the image storage (WS-IM) 4f.

3.4.3) The control of the workstation WS-1 references the interpretation reference priority information, transfers an examination ID number (103541) of an examination having the highest reference priority to the network interface 4j, then instructs the network interface 4j to issue an image transfer request to the database. The network interface sends the received examination ID number and an image request command to the database (DB) 3.

3.4.4) When the examination ID number and image request command reaches the network interface (DB-NWIF)

3h of the database 3, the control (DB-CTRL) 3a of the database 3 reads out the received data from the network interface 3h, then writes the data in system memory of the control 3a.

3.4.5) The control 3a of the database 3 checks if the image data and additional information data specified with the received examination ID number reside on the image storage magnetic disk (DB-IHD) 3f. If the data resides, the control 3a reads out all image data and additional data involved in the examination having the examination ID number, then sends the data to the workstation WS-1 via the network interface 3h. Two chest plain X-ray images are involved in the examination of the examination ID number 103541. There is a very high probability that the image data and additional information data of the two images reside on the image storage magnetic disk.

If the data has been deleted from the image storage magnetic disk 3f for some reason, the control 3a instructs the information search unit 3d to read out examination directory data specified with the examination ID number from the examination directory storage 3c, then calculates the addresses of image data and additional information data on the image storage optical disk 3e. Then, the control 3a reads out the image data and additional information data from the image storage optical disk 3e, then sends the data to the workstation WS-1 via the network interface 3h.

3.4.6) When the image data and additional information data the database 3 has sent reaches the network interface 4j of the workstation WS-1, the control 4a of the workstation WS-1 reads out the received data from the network interface 4j, then writes the data in the image storage (WS-IM) 4f.

3.4.7) Using the aforesaid procedure, the control 3a of the database 3 requests the database 3 to transfer image data and additional data concerning other examinations specified in the interpretation reference priority information, then writes the data in the image storage 4f. Image requests are issued to the database 3 in order of reference priorities. Therefore, images involved in previous examinations are handled in the order of the examination ID numbers 100902, 102287, and 60563 to obtain the image data and additional information data.

4. Executing CAD Processing and Creating Diagnostic Information (1) CAD processing The workstation 4 performs CAD processing on any ones of all images acquired in four examinations to which CAD processing can apply. It is highly probable that the CAD processing is carried out before interpretation. This is because the current technology makes it possible to load images into a workstation in several minutes after image acquisition during an examination, but the images acquired in the examination are usually interpreted much later.

4.1.1) The control (WS-CTRL) 4a of the workstation WS-1 references abnormality detection means select information (Table 11) to determine whether CAD processing can apply to each of two images acquired during an interpretation examination (examination ID number 103541). Specifically, the control 4a checks if the combination of the examined region, modality, and examination procedure existent in the examination information data resides in the abnormality detection means select information. As apparent in Tables 18, 19, and 11, as far as the examination having the examination ID number 103541 is concerned, only an image of an image number 1 is a frontal image to which CAD processing can apply. The types of detectable abnormalities are pulmonary interstitial disease and pulmonary nodules.

4.1.2) The control 4a of the workstation WS-1 reads out an image having an image number 1 acquired in an examination having an examination ID number 103541 from the image storage (WS-IM) 4f, then inputs the image to the CAD processor (WS-CADP) 4e together with data indicating detection of "pulmonary interstitial disease." The control 4a also instructs the CAD processor 4e to output the positions of normal anatomical structures. The CAD processor 4e activates the pulmonary interstitial disease detection means to the input image data, then analyzes the image data. The analyzed data of the positions and degrees of abnormalities, and the positional data of normal anatomical structures or image evaluation areas are stored in internal memory of the CAD processor 4e.

4.1.3) The control 4a of the workstation WS-1 reads out the image having the image number 1 acquired in the examination having the examination ID number 103541 from the image storage 4f, then inputs the image to the CAD processor 4e together with data indicating "pulmonary nodules" detection.

The CAD processor 4e activates the pulmonary nodule detection means to the input image data, and thus analyzes the image data. The analyzed data of the positions and degrees of abnormalities is stored in internal memory of the CAD processor 4e.

4.1.4) The control 4a of the workstation WS-1 checks the images acquired in three examinations of examination ID numbers 100902, 102287, and 60563 to see if any abnormality detection means can apply to the images. If applicable abnormality detection means are available, all the applicable abnormality detection means are activated to detect abnormalities under the CAD processor 4e. Each image to which CAD processing applies is processed once to determine the positions of normal anatomical structures or image evaluation areas.

Assuming that two images acquired in a chest plain Xray examination having an examination ID number 100902 are frontal (image number 1) and left lateral image (image number 2), the frontal image is handled to detect pulmonary interstitial disease and pulmonary nodules.

The examined region in an examination having an examination ID number 102287 is the right foot. Therefore, all the images acquired in the examination are not subjected to CAD.

The examined region in an examination having an examination ID number 60563 is the brain, and the modality, CT. Therefore, all the images acquired in the examination are not subjected to CAD.

CAD processing applies to examinations in order of reference priorities specified in interpretation reference priority information.

Table 22 lists the data values indicating the positions and degrees of abnormalities stored in internal memory of the CAD processor 4e.

TABLE 22

Example of data values indicating the positions and
degrees of abnormalities CAD processing provides (abnormality data table)

| Ref. No. | Examination ID No. | Image No. | Type of Abnormality | Center position of an abnormality on an image (X and Y coordinates) | Degree or size (cm) | Area containing an abnormality |
|---|---|---|---|---|---|---|
| 1 | 103541 | 1 | Pulmonary interstitial disease | (350,1350) | 9 | |
| 2 | 103541 | 1 | Pulmonary interstitial disease | (400,1500) | 8 | |
| 3 | 103541 | 1 | Pulmonary interstitial disease | (300,1600) | 8 | |
| 4 | 103541 | 1 | Pulmonary interstitial disease | (1600,1300) | 8 | |
| 5 | 100902 | 1 | Pulmonary interstitial disease | (350,1350) | 7 | |
| 6 | 100902 | 1 | Pulmonary interstitial disease | (400,1500) | 7 | |
| 7 | 100902 | 1 | Pulmonary nodules | (1500,800) | 1 | |

In Table 22, degrees of pulmonary interstitial disease are expressed with numerals ranging from 1 to 10. If the type of abnormality is pulmonary nodules, the degree is represented as the diameter of a nodule (cm). Data indicating an area containing an abnormality has not been created at this stage. Therefore, the column is blank. The data of Table 22 shall be referred to as an "abnormality data table" for easy understanding.

Figure 17:
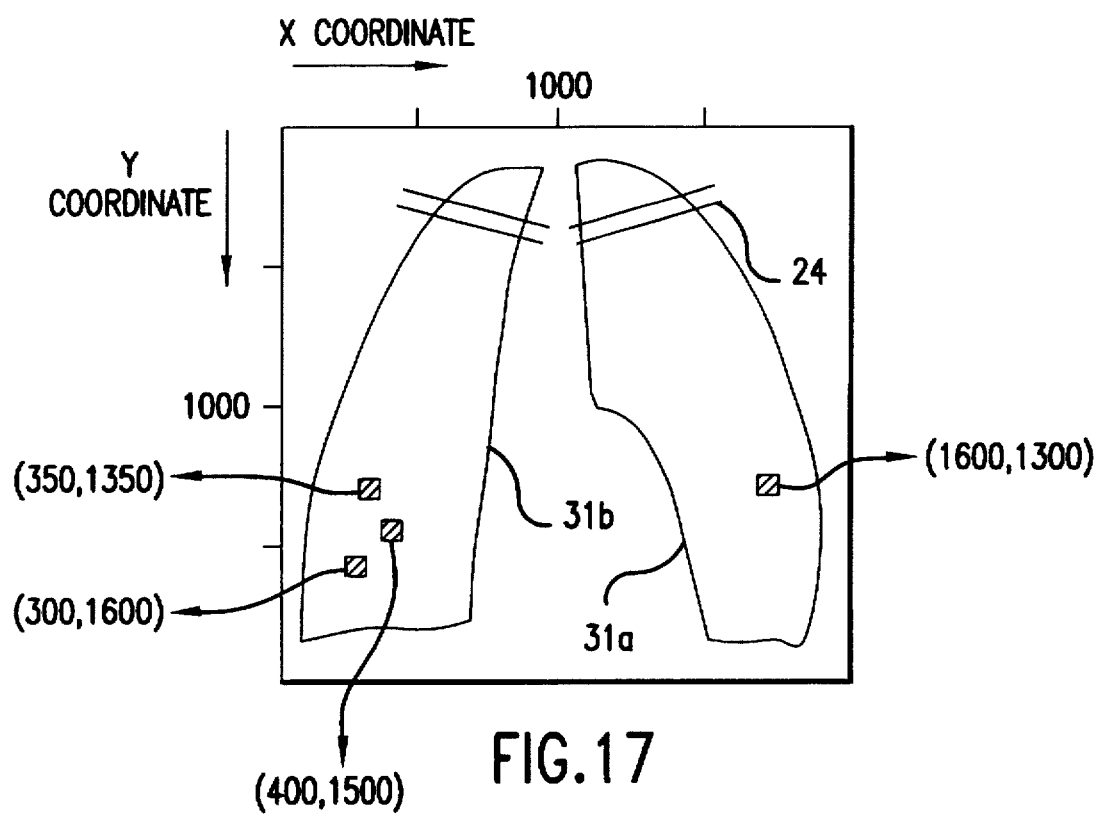
FIG. 17 shows an image associated with part of Table 22 "Abnormality data table"
Figure 18:
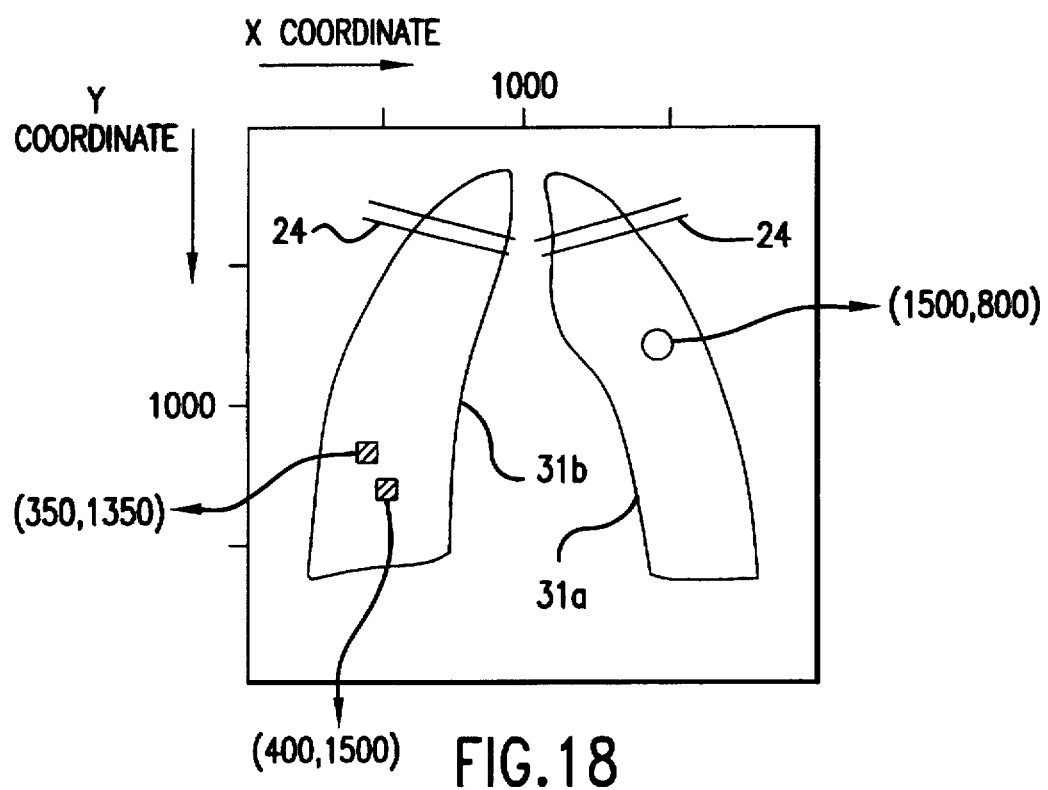
FIG. 18 shows an image associated with part of Table 22 "Abnormality data table"

FIGS. 17 and 18 show images indicating the center positions of abnormalities listed in Table 22. FIG. 17 shows an image specified with an examination ID number 103541 (image number 1), and FIG. 18, an image specified with an examination ID number 100902 (image number 1). In FIGS. 17 and 18, 31a and 31b denote the left and right lung fields as shown in FIG. 10. 24 denotes the costa.

Table 23 lists the positional data values of normal anatomical structures or image evaluation areas. Referencing FIGS. 17 and 18 will help understand the contents of Table 23.

TABLE 23

Example of the positional data values of normal anatomical
structures or image evaluation areas CAD processing
provides (area data table)

| Examination No. | Image No. | Border of areas in an image | Position of the border |
|---|---|---|---|
| 103541 | 1 | Center line between the left and right lung fields | X coordinate 1000 |
| 103541 | 1 | Border between the superior and central lung fields | Y coordinate 700 |
| 103541 | 1 | Border between the central and inferior lung fields | Y coordinate 1200 |
| 100902 | 1 | Center line between the left and | X coordinate 1000 |

TABLE 23-continued

Example of the positional data values of normal anatomical
structures or image evaluation areas CAD processing
provides (area data table)

| Examination No. | Image No. | Border of areas in an image | Position of the border |
|---|---|---|---|
| 100902 | 1 | right lung fields Border between the superior and central lung fields | Y coordinate 700 |
| 100902 | 1 | Border between the central and inferior lung fields | Y coordinate 1200 |

In Table 23, the positional data corresponds to the position of a border (position of a border between image evaluation areas). Using the data, an area in which a certain abnormality reside can be identified. From this viewpoint, the position of a border is equivalent to the positional data. In this embodiment, abnormalities are detected only in the lung fields in an image. The data of Table 23 shall be referred to as an "area data table" for easy understanding.

(2) Identifying lung field areas containing abnormalities 4.2.1) The control (WS-CTRL) 4a of the workstation WS-1 references the positional data of normal anatomical structures or image evaluation areas specified in an area data table for each abnormality specified in the abnormality data table, then identifies image evaluation areas to which the positions of abnormalities belong. Data indicating areas is written in the abnormality data table. The abnormality data table is read out from the internal memory of the CAD processor 4a into the system memory of the control 4a, then processed according to the procedure described below. Then, the updated abnormality data table is written in the image storage (WS-IM) 4f.

(a) Data whose examination ID number and image number agree with those relative to a certain abnormality is extracted from the area data table.

(b) The X coordinate of the position of the abnormality is compared with the X coordinate of the center line between the left and right lungs. If the X coordinate of the position of the abnormality is smaller than that of the center line between the left and right lungs, the position of the abnormality is thought to belong to the right lung field. If the X coordinate of the position of the abnormality is larger, the position of the abnormality is thought to belong to the left lung field. This is because a frontal image this embodiment defines represents only an image acquired by projecting an X-ray from a patient's back. In this image, the left side of an image visualizes the right lung field, and the right side, the left lung field.

An image acquired by projecting an X-ray from a patient's frontal is also a frontal image, to which CAD processing can apply. In this case, image data specifying the imaging direction "A to P" is handled and the positions of the left and right lung fields are reversed. The left and right lung fields are differentiated by referencing the imaging direction data existent in additional information.

(c) The Y coordinate of the position of the abnormality is compared with that of the border between the superior and central lung fields. If the Y coordinate of the position of the abnormality is smaller, the position of an abnormality is determined to belong to the superior lung field.

(d) If the Y coordinate of the position of the abnormality is larger than or equal to that of the border, the Y coordinate of the position of the abnormality is compared with that of the border between the central and inferior lung fields. If the Y coordinate of the position of the abnormality is smaller, the abnormal position is determined to belong to the central lung field. If the Y coordinate of the position of the abnormality is larger than or equal to that of the border, the position of the abnormality is determined to belong to the inferior lung field.

(e) Data indicating the determined left or right, or superior, central, or inferior lung field is written in the abnormal data table in association with the position of the abnormality.

The foregoing procedure is executed repeatedly for all abnormalities specified in the abnormality data table. Table 24 is the abnormality data table when the repeated execution of the procedure is complete. In Table 24, data indicating a lung field area is expressed, for example, as (lung field, right, inferior) which means the right inferior lung field. This is true for other expressions.

TABLE 24

Example of data values in a completed abnormality data table

| Ref. No. | Examination ID No. | Image No. | Type of Abnormality | Center position of an abnormality in an image (X and Y coordinates) | Degree or size (cm) | Area containing an abnormality |
|---|---|---|---|---|---|---|
| 1 | 103541 | 1 | Pulmonary interstitial disease | (350,1350) | 9 | (lung field, right, inferior) |
| 2 | 103541 | 1 | Pulmonary interstitial disease | (400,1500) | 8 | (lung field, right, inferior) |
| 3 | 103541 | 1 | Pulmonary interstitial disease | (300,1600) | 8 | (lung field, right, inferior) |
| 4 | 103541 | 1 | Pulmonary interstitial disease | (1600,1300) | 8 | (lung field, left, inferior) |
| 5 | 100902 | 1 | Pulmonary interstitial disease | (350,1350) | 7 | (lung field, right, inferior) |
| 6 | 100902 | 1 | Pulmonary interstitial disease | (400,1500) | 7 | (lung field, right, inferior) |
| 7 | 100902 | 1 | Pulmonary nodule | (1500,800) | 1 | (lung field, left, central) |

(3) Creating a time-sequential abnormality change data table 4.3.1) The control (WS-CTRL) 4a of the workstation WS-1 uses data existent in an abnormality data table to create a "time-sequential abnormality change data table." The time-sequential sequential abnormality change data table has a listing form shown in Table 25.

TABLE 25

Example of data values indicating time-sequential abnormality changes (time-sequential abnormality change data table)

| Ref. No. | Examination ID No. | Image No. | Type of Abnormality | Center position of an abnormality in an image | Area containing an abnormality | Abnormality change | Abnormality change rate (cm) | Examination ID No. of a previous image | Image No. of a previous image |
|---|---|---|---|---|---|---|---|---|---|
| 1 | 103541 | 1 | Pulmonary interstitial disease | (350, 1350) | (lung field, right, inferior) | Progress | +2 | 100902 | 1 |
| 2 | 103541 | 1 | Pulmonary interstitial disease | (400, 1500) | (lung field, right, inferior) | Progress | +1 | 100902 | 1 |
| 3 | 103541 | 1 | Pulmonary interstitial disease | (300, 1600) | (lung field, right, inferior) | Onset | +8 | 100902 | 1 |
| 4 | 103541 | 1 | Pulmonary interstitial disease | (1600, 1300) | (lung field, left, inferior) | Onset | +8 | 100902 | 1 |
| 5 | 103541 | 1 | Pulmonary nodule | (1500, 800) | (lung field, left, central) | Fading | −1 | 100902 | 1 |

The data values contained in the table are created according to the following procedure:

(a) As for certain abnormality data detected in an image of an interpretation examination, the examination ID number, image number, type of abnormality, position of the abnormality in an image, and area containing the abnormality are written in a time-sequential abnormality change data table.

(b) A search is made for other abnormality data (comparison data) specifying the same type of abnormality and same position as the abnormality data detected in the image acquired in the interpretation examination.

If comparison data is not found, data "Onset" is specified in the data item "Abnormality change." The abnormality change rate is represented as a difference of the degree specified in the abnormality data of an interpretation image (Ab1) minus the degree in the comparison data (Ab2); that is, Ab1−Ab2. Herein, since Ab2 is defined as 0, the difference will be Ab1.

The examination ID number and image number specified for any examination other than the interpretation examination in the abnormality data table are used as the values for "Examination ID number of a previous examination" and "Image number of a previous image."

(c) If comparison data is found, the degree specified in the abnormality data of an interpretation image is compared with that in the comparison data.

(1) If the degree in the abnormality data of the interpretation image is higher than that in the comparison data, "In progress" is specified in "Abnormality change."

(2) If the degree in the abnormality data of the interpretation image is equal to that in the comparison data, "Unchanged" is specified in "Abnormal change."

(3) If the degree in the abnormal data of the interpretation image is lower than that in the comparison data, "Recovered" is specified in "Abnormal change."

In any case, the examination ID number and image number specified in the comparison data are used as the values for "Examination ID number of a previous examination" and "Image number of a previous image."

In any case, the abnormality change rate is represented as a difference of the degree specified in the abnormal data of an interpretation image (Ab1) minus the degree in the comparison data (Ab2); that is, Ab1−Ab2.

(d) The procedure of the above steps (a), (b), and (c) is performed on all other abnormality data detected in the image acquired in the interpretation examination.

(e) If any abnormality data has not served as comparison data so far, the data is subjected to the following operations:

(1) The type of abnormality, position of the abnormality in an image, and area containing the abnormality specified in the comparison data are written in the time-sequential change data table.

(2) The examination ID number and image number specified in the comparison data are written as the examination ID number of a previous examination and the image number of a previous image in the time-sequential change data table.

"Fade-out" is written as the abnormality change. The abnormality change rate is represented as a difference of the degree specified in the abnormality data of an interpretation image (Ab1) minus the degree in comparison data (Ab2); that is, Ab1−Ab2. Herein, since Ab1 is defined as 0, the abnormality change rate comes to −Ab2.

The examination ID number of the interpretation examination is written in "Examination ID number," and the image number of an image acquired in the same imaging direction during the interpretation examination, in "Image number."

The thus-created time-sequential abnormality change data table (Table 25) is written in the image storage 4f.

(4) Creating overlay display information for indicating abnormalities 4.4.1) Creating overlay display information for indicating time-sequential abnormality changes The control (WS-CTRL) 4a of the workstation WS-1 creates a time-sequential abnormality change data table. Then. the control 4a creates "overlay display information" for indicating the positions and time-sequential abnormality changes of abnormalities and stores the created overlay display information in the image storage (WS-IM) 4f.

Table 26 lists the created overlay display information.

TABLE 26

Example of overlay display information for displaying time-sequential abnormality changes

| Data No. | Type of graphic | Size of graphic (mm) | Coordinates (X, Y) | Display color | Flickering control information |
|---|---|---|---|---|---|
| 1 | Arrow | 10 | (350,1350) | Yellow | No flickering |
| 2 | Arrow | 10 | (400,1500) | Yellow | No flickering |
| 3 | Arrow | 10 | (300,1600) | Red | No flickering |
| 4 | Arrow | 10 | (1600,1300) | Red | No flickering |
| 5 | Arrow | 10 | (1500,800) | Blue | No flickering |

The overlay display information indicating time sequential abnormality changes is associated with images. The overlay display information in Table 26 indicates time-sequential changes of abnormalities detected in an image having an image number 1 acquired in an examination having an examination ID number 103541. The data numbers in Table 26 are assigned for convenience sake.

Positions of abnormalities are indicated with arrows, and time-sequential abnormality changes, with different colors of arrows. The data contained in this table is created according to the following procedure:

(a) The control 4a of the workstation WS-1 retrieves the data of positions of abnormalities in an image and time-sequential abnormality changes from the abnormality data specified with a reference number 1 in the time-sequential abnormality change data table. "Arrow" is written as the type of graphic in a data number 1 of overlay display information, and "10 mm", as the size of a graphic. The type of graphic and the size of a graphic are common among all abnormality change data. The coordinates specified in the time-sequential abnormality change data table are copied in "Coordinates (X, Y)."

(b) The control 4a of the workstation WS-1 references the relational information between time-sequential abnormality changes and display colors (Table 12), then determines a display color. In this case, the timesequential abnormality change is "In progress." Therefore, the display color is yellow. Then, "Yellow" is written as the display color in the data number 1 of overlay display information.

(c) "No flickering" is always written as flickering control information at this stage.

(d) The operations of (a) to (c) are performed on the abnormalities of other reference numbers. However, since an overlay is superimposed on an image, only abnormalities specified with the same examination number and same image number are written in the same overlay display information. In this embodiment, all time-sequential change data is written in the same overlay display information.

(e) The control 4a of the workstation WS-1 associates the created overlay display information with the examination numbers and image numbers, then stores the associated data in the image storage 4f.

4.4.2) Creating overlay display information indicating the results of detecting abnormalities in images The control (WS-CTRL) 4a of the workstation WS-1 references an abnormality data table, creates overlay display information indicating positions and degrees of abnormalities. then stores the created overlay data in the image storage (WS-IM) 4f.

Tables 27 and 28 show examples of created overlay display information. Table 27 relates to an image having an image number 1 acquired in an examination ID number 103541, and Table 28, an image having an image number 1 acquired in an examination ID number 100902. The data numbers in Tables 27 and 28 are assigned for convenience sake.

TABLE 27

Example of overlay display information for indicating the results of detecting abnormalities in an image

| Data No. | Type of graphic | Size of a graphic (mm) | Coordinates | Display color | Flickering control information |
|---|---|---|---|---|---|
| 1 | Arrow | 9 | (350,1350) | White | No flickering |
| 2 | Arrow | 8 | (400,1500) | White | No flickering |
| 3 | Arrow | 8 | (300,1600) | White | No flickering |
| 4 | Arrow | 8 | (1600,1300) | White | No flickering |

TABLE 28

Example of overlay display information for indicating the results of detecting abnormalities in an image

| Data No. | Type of graphic | Size of a graphic (mm) | Coordinates | Display color | Flickering control information |
|---|---|---|---|---|---|
| 1 | Arrow | 7 | (350,1350) | White | No flickering |
| 2 | Arrow | 7 | (400,1500) | White | No flickering |
| 3 | Arrow | 10 | (1500,800) | White | No flickering |

Positions of abnormalities are indicated with arrows, and sizes of abnormalities, with arrow lengths. A longer arrow indicates a larger abnormality. The arrows are shown in white.

The data values contained in the above table are created according to the following procedure:

(a) The control 4a of the workstation WS-1 reads out the date indicating the position in an image and degree of the abnormality having a reference number 1 from the abnormality data table (Table 22). "Arrow" is written as the type of graphic for a data number 1 in overlay display information. The coordinates specified in the time-sequential abnormality change table are written in "Coordinates." The type of graphic is common among all abnormality change data.

(b) The control 4a of the workstation WS-1 assesses the degree to determine the length of an arrow. An abnormality with a degree N is indicated with an arrow of N mm long. Then, "N mm" is written as the size of the graphic.

(c) The display color is determined as white. Therefore, "White" is written as the display color.

(d) "No flickering" is always written as flickering control information at this stage.

(e) The operations (a) to (d) are performed on the abnormalities of other reference numbers. However, since overlay display information is superimposed on an image, only abnormalities specified with the same examination number and image number are written in the same overlay display information data. In this embodiment, four sets of data concerning the abnormalities of reference numbers 1 to 4 in Table 24 are combined to create single overlay display information (Table 27). Then, three sets of data concerning the abnormalities of reference numbers 5 to 7 are combined to create other overlay display information (Table 28).

(f) The control 4a of the workstation 4 associates the created overlay display information with the examination and image numbers, then stores the associated data in the image storage 4f.

5. Interpreting Images and Entering an Interpretation Report by an Interpreting Doctor A workstation is generally provided with multiple patients' images. When interpreting images, an interpreting doctor is usually indifferent to the order of interpreting patients' images. Therefore, the workstation automatically determines the order of interpreting images, so that images are interpreted, for example, in order of dates of examination.

Assuming that an interpreting doctor uses a workstation WS-1 to interpret images acquired in a chest plain X-ray examination (examination ID number 103541) performed on a patient T. Suzuki (patient ID number 870802), then creates an interpretation report, the operations will be described below.

(1) Displaying data for image interpretation 5.1.1) Loading data

First of all, required data is loaded according to the following procedure:

(a) Reading an examination history

The control (WS-CTRL) 4a of the workstation WS-1 reads out examination history data specified with a patient ID number 870802 from the image storage (WS-IM) 4f, then writes the read data in system memory of the control 4a.

(b) Reading additional information and image data

The control 4a of the workstation WS-1 references interpretation reference priority information, reads out additional information of all images (two images in this example) specified with an examination ID number (103541) and a priority 0 from the image storage 4f, then writes the read data in system memory of the control 4a.

All images (two images in this example) specified with an examination ID number (100902) and a priority 1 are read out from the image storage 4f and written in an image frame memory (WS-IFM) 4g.

Next, the additional information of all images specified with examination ID numbers (100902, 102287, and 60563) and priorities 1, 2, and 3 is read out from the image storage 4f, then written in system memory of the control 4a. All image data is read out from the image storage 4f, then written in the image frame memory 4g.

What is important here that image data reading is proceeds in order of interpretation reference priorities. Thereby, even if the number of images acquired from a patient is too large to be fully written in the image frame memory 4g, the data of images having higher possibilities of being referenced are placed in image frame memory.

(c) Reading interpretation reports The control 4a of the workstation WS-1 references interpretation reference priority information, reads out interpretation reports from the image storage 4f in order of priorities (in the order of examination ID numbers 10354, 100902, 102287, and 60563), then writes the read data in system memory of the control 4a.

(d) Reading out a time-sequential abnormality change data table

The control 4a of the workstation WS-1 reads out the time-sequential abnormality change data table created immediately before (Table 25) from the image storage 4f, then writes the data in system memory of the control 4a.

(e) Reading out an abnormal data table

The control 4a of the workstation WS-1 reads out an abnormality data table (Table 24) created immediately before from the image storage 4f, then writes the data in system memory of the control 4a.

(f) Reading out overlay display information for indicating time-sequential abnormality changes The control 4a of the workstation WS-1 references the time-sequential abnormality change data table existent in system memory, reads out overlay display information for indicating time-sequential abnormality changes stored in association with the combinations of examination ID numbers (data item next to the reference number in Table 25) and image numbers from the image storage 4f, then writes the read data in system memory of the control 4a. In this example, only overlay display information associated with the examination number 103541 and image number 1 is read out.

(g) Reading out overlay display information for indicating the results of detecting abnormalities in images The control 4a of the workstation WS-1 references the abnormality data table (Table 24) existent in system memory, reads out overlay display information for indicating the results of detecting abnormalities stored in association with the combinations of image ID numbers and image numbers from the image storage 4f, then writes the read data in system memory of the control 4a. In this example, overlay display information associated with the combination of an examination number 103541 and an image number 1 and other overlay display information associated with the combination of an examination number 100902 and an image number 1 are read out.

5.1.2) Displaying images

A workstation WS-1 displays the images for an interpretation examination. Four displays (WS-IDISP) 4i are available, making it possible to simultaneously display two images for an interpretation examination (examination ID number 103541) and two images acquired in other examination (examinations ID number 100902) which are most likely to be referenced. This automatic display procedure is proceeded as follows:

(a) The control 4a of the workstation WS-1 first references the additional information of two images specified with an examination ID number 103541 and becomes aware of the imaging directions of the images; that is, P to A (frontal image) and R to L (left lateral image) (See Table 19). Next, the display position determining means 4m determines the relative display positions in light of the relational information table between the imaging directions of chest plain X-ray images and the relative display positions (Table 13). Consequently, an image (frontal image) acquired in an imaging direction P to A appears on the leftmost one of four image displays lined sideways, and an image (left lateral image) acquired in an imaging direction R to L, on a display on the right of the one for the P-to-A image.

(b) The control 4a of the workstation WS-1 references the additional information of two images specified with an examination ID number 100902 and becomes aware of the imaging directions. Assume that the imaging directions are P to A (frontal image) and R to L (left lateral image). The display position determining means 4m determines the relative display positions in light of the relational information table between the imaging directions of chest plain X-ray images and the relative display positions (Table 13). Consequently, an image (frontal image) acquired in an imaging direction P to A appears on the third on the left among four image displays 4i lined sideways, and an image acquired in an imaging direction R to L, on an image (left lateral image) display on the right of the image display for an P-to-A image.

Figure 19:
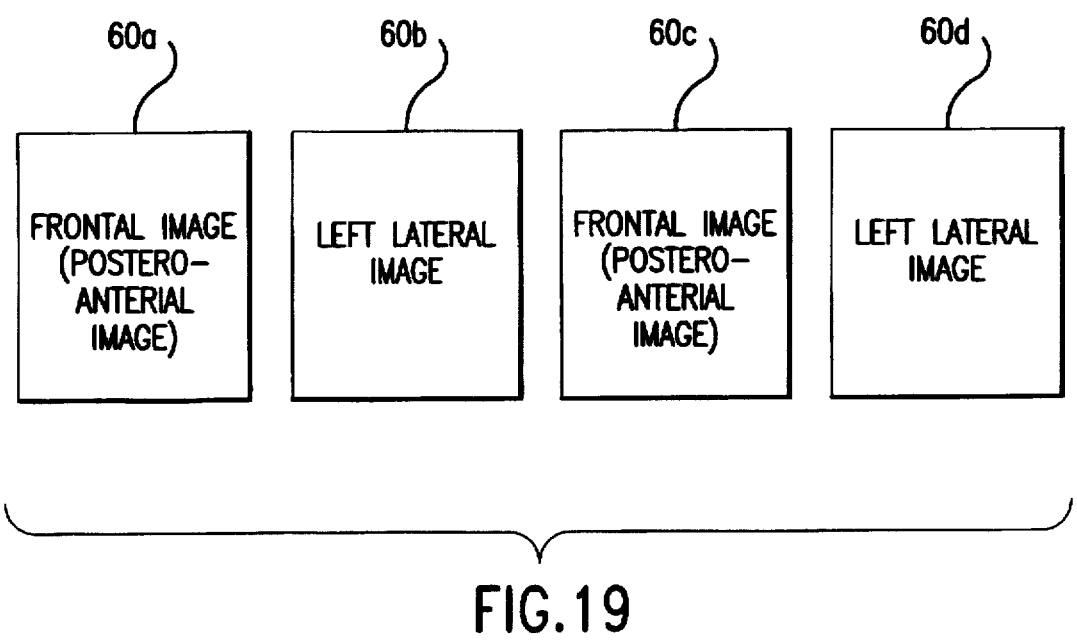
FIG. 19 shows the relationships between the image display of a workstation and the types of images displayed at the start of interpretation.

FIG. 19 shows the relationships between image displays 4i and types of displayed images. 60a, 60b, 60c, and 60d denote images from left sequentially, which are displayed on four image displays 4i lined sideways.

According to the foregoing relationships between the image displays 4i and types of images, the image 60a and image 60b represent images for an interpretation examination (chest plain X-ray images acquired in an examination of an examination ID number 103541). Herein, the image 60a is a frontal image, and the image 60b, a left lateral image. On the other hand, the image 60c and image 60d represent images acquired in a previous examination (chest plain X-ray images acquired in an examination of an examination ID number 100902), wherein the image 60c is a frontal image, and the image 60d, a left lateral image.

When an image is displayed on an image display 4i, the examination ID number of the relevant examination and the image number within the examination (both of which reside in additional information) are displayed.

5.1.3) Displaying examination request information

The control (WS-CTRL) 4a of the workstation WS-1 fetches predetermined data including a purpose of examination, clinical information, and disclosed diseases from among examination request information which is read into system memory immediately before, then displays the data on the character display (WS-CDISP) 4d.

5.1.4) Displaying an examination history

The control (WS-CTRL) 4a of the workstation WS-1 fetches predetermined data from among examination history data which is read into system memory immediately before, then displays the data on the character display 4d.

The control 4a of the workstation WS-1 numbers examinations in an examination history in descending order of dates of examination, then displays the examinations. The control 4a references interpretation reference priority information to select an examination with a priority 0 (interpretation examination whose relevant images are uninterpreted), then marks the examination number in the displayed examination history with a leading black star ★. As for an examination with a priority 1 (examination which is most likely to be referenced), the examination number in the displayed examination history is marked with a leading white star ☆. Thereby, an interpretation examination and an examination which is most likely to be referenced are discernible at sight.

FIG. 20 shows an examination history displayed on the character display 4d. In FIG. 20, 61 denotes a CRT screen of a character display 4d.

5.1.5) Displaying a previous interpretation report

The control 4a of the workstation WS-1 selects an interpretation report specified with an examination number with the highest interpretation reference priority from among the patient's previous interpretation reports which are read into system memory immediately before, then displays the report on the character display 4d.

Then, an interpreting doctor reads the interpretation report displayed. To display another image or interpretation report than the displayed one, the doctor must enter a specific command at the input unit (WS-INPUT) 4c.

(2) Entering an interpretation report by an interpreting doctor

When completing image interpretation, the doctor enters an interpretation report at the workstation. The input unit 4c is used for the entry, and the character display 4d, for the display. An interpretation report is entered by selecting words, clauses, and sentences. Words, clauses, and sentences to be selected are pre-registered with the system disk in the control 4a of the workstation. The dictionary is shared within the system.

5.2.1) Displaying an interpretation report creation screen

When the interpreting doctor enters an interpretation report creation command at the input unit 4c of the workstation WS-1, the control 4a of the workstation WS-1 displays a format of an interpretation report on the character display 4d.

FIG. 21 shows a format of an interpretation report displayed on a screen of the character display 4d. In FIG. 21, an area enclosed with a dotted line is an area for displaying words, clauses, and sentences to be selected by an interpreting doctor. 61 denotes a CRT screen of a character display 4d.

5.2.2) Entering an interpretation report

The interpreting doctor enters the items below for each finding according to the displayed format.

(1) Type of abnormality (2) Area containing an abnormality (3) Result of comparing with a previous image (4) Examination ID number relative to a previous image compared (5) Image number of a previous image compared The examination ID number of a previous examination compared and the image number relative to a previous examination compared shall be the numerical values displayed together with the image. If a specific finding is provided by interpreting an image without comparing with a previous image, 0 is entered as an examination ID number of a previous image compared. The control 4a displays the entered data at predetermined positions on a screen, then stores the data in association with the finding numbers in system memory.

FIG. 22 shows the finding displayed on a screen at this stage. 61 denotes a CRT screen of the character display 4d.

Table 29 lists the finding data written in system memory.

TABLE 29

Example of findings in an interpretation report written in internal memory of a workstation

| Finding No. | Type of abnormality | Area containing an abnormality | Result of comparing with a previous image | Image No. in an interpretation examination | Examination ID No. of a previous image compared | Image No. of a previous image compared |
|---|---|---|---|---|---|---|
| 1 | Pulmonary interstitial disease | (lung, right, inferior) | In progress | 1 | 100902 | 1 |
| 2 | Enlarged cardiac shadow | (heart) | Onset | 1 | 100902 | 1 |

When FIG. 22 and Table 29 are compared, a difference is found. Specifically, although the interpreting doctor selects a word "right inferior lung field" as an area containing an abnormality for a finding 1, "lung field, right, inferior" is written for the finding in system memory. The word "right inferior lung field" is displayed as a selective word. However, in the internal dictionary, data "lung field, right, inferior" is stored in association with the word "right inferior lung field."

A word "Discovered" in the entered finding is replaced by "Onset."

After completing entry of findings, the interpreting doctor enters a conclusion.

The interpreting doctor enters an interpretation report input termination command at the input unit 4c.

6. Comparing Diagnostic Information and Calling Interpreting Doctor's Attention (1) Extracting comparison findings from an interpretation report Findings to be compared with diagnostic information resulting from CAD processing are picked up from among findings in an interpretation report.

The control (WS-CTRL) 4a of the workstation WS-1 checks findings in an interpretation report for the combination of data items below to see if their data values are found in abnormal detection means select information, then extracts findings whose data values agree with the values existent in the abnormal detection means select information.

1. Type of abnormality (existent in a finding of an interpretation report)
2. Examined region in an interpretation examination (existent in an examination history)
3. Modality (existent in an examination history)
4. Examination procedure (existent in an examination history)
5. Imaging direction (imaging direction of an image having an image number in an interpretation examination existent in a finding in an interpretation report, which is specified in additional information)

In this embodiment, a finding of a finding number 1 in Table 29 is extracted.

(2) Comparing an interpretation report with an abnormality data table and attracting attention The control (WS-CTRL) 4a of the workstation WS-1 compares each finding in an interpretation report extracted by the foregoing operation (1) with each data in an abnormality data table according to the following procedure:

(a) The control 4a reads "Examination ID number of a previous examination compared" in the interpretation report, and determines whether the finding results from interpretation of only an interpretation image. More particularly, the control 4a checks if 0 is specified as the examination ID number of the previous examination compared.

(b) If 0 is specified, the control 4a of the workstation WS-1 compares the finding in the interpretation report with the abnormalities in the abnormality data table (Table 22) in terms of four data items listed below, then extracts abnormalities whose relevant data values agree with those of the finding.

1. Type of an abnormality
2. Area containing an abnormality
3. Examination ID number of an interpretation examination (which is not entered for the finding in an interpretation report, but can be derived from an examination history)
4. Image number relative to an interpretation examination Herein, as for the abnormalities extracted from the abnormality data table at this step, the interpreting doctor's findings are consistent with the CAD results.

(c) If 0 is not specified as the examination ID number, the operations of the steps (a) and (b) are executed for other findings extracted from the interpretation report by performing the operation (1).

(d) At this stage, when abnormalities specified in findings extracted by the operation (1) are compared with those specified in the abnormality data table, if the data values agree mutually, the interpreting doctor's findings are thought to be consistent with the results of CAD processing. Then, the subsequent steps are not executed.

As for the abnormalities specified in findings in the interpretation report and in the abnormality data table whose data value disagree mutually, the interpreting doctor's findings are thought to be inconsistent with the results of CAD processing. Inconsistency may occur in any of the following two cases:

Case 1: an interpreting doctor recognizes normality (no finding), while CAD detects an abnormality.

Case 2: an interpreting doctor identifies an abnormality, while CAD fails to detect an abnormality.

The control 4a of the workstation WS-1 reads out inconsistent findings and abnormality data from the interpretation report and abnormality data table, then stores them separately.

(e) When abnormality data belonging to the foregoing case 1 is found, the control 4a takes the following actions:

1. Outputting a peep sound
2. Displaying a message "CAD points out an abnormality unfound in the finding," in a terminology display area in the portion of the character display (WS-CDISP) 4d for displaying a created interpretation report.
3. Displaying the image detecting the abnormality data belonging to the case 1 on the image display (WS-IDISP) 4d.
4. Superimposing overlay data indicating the results of detecting abnormalities on the image.
5. Flickering the arrow of an abnormality relevant to the case 1 without flickering the other arrows overlaid. This is the only time when the control 4a modifies the value of flickering control information existent in overlay display information to "Flickering." Then, the control 4a transmits the modified data to the image display manager 4h.

In the case 2, an interpreting doctor's attention is not called. This is because the current CAD technology creates areas in an image in which no abnormality can be detected. An interpreting doctor may identify an abnormality in any of the areas. With the advancement of the technology, such areas in which no abnormality can be detected will become inexistent. Then, an interpreting doctor's attention will be called in the case 2. That is to say, a message indicating a finding number and attracting attention; such as, "Finding 1: CAD points out normality," will be displayed in the terminology display area in the portion of the character display 4d for displaying an interpretation report.

In this embodiment, an interpretation report does not contain findings resulting from interpretation of only interpretation images. Therefore, the operations of the steps (d) and (e) are not carried out.

(3) Comparing an interpretation report with a time-sequential abnormality change data table and attracting attention The control (WS-CTRL) 4a of the workstation WS-1 compares each of the findings extracted from an interpretation report by the operation (1) with a time-sequential change data table according to the following procedure:

(a) The control 4a reads "Examination ID number of a previous examination compared" from the interpretation report, and determines whether a finding is derived from comparison with an image in a previous examination. More particularly, the control 4a checks if 0 is specified as the examination ID number of a previous examination compared.

(b) If 0 is not specified, the control 4a of the workstation WS-1 compares the finding in the interpretation report with abnormalities in the time-sequential abnormality data table in terms of the six data items described below, then extracts abnormalities whose relevant values agree with those of the finding from the time-sequential abnormality data table.

1. Type of abnormality
2. Are a containing an abnormality
3. Examination ID number of a n interpretation examination (which is not entered in the finding in the interpretation report but easily found in an examination history)
4. Image number in an interpretation examination
5. Examination ID number of a previous examination compared
6. Image number of a previous image compared For the abnormality changes extracted from the time-sequential abnormality change data table, the interpreting doctor can have pointed out the changes of the abnormalities. In this embodiment, time-sequential change data of reference numbers 1, 2, and 3 in Table 25 is extracted.

(c) Next, the abnormality change rates of the abnormalities extracted at the step (b) are assessed totally. Then, th e result is compared with the value in "Result of comparing with a previous image" for the finding in the interpretation report to see if they agree. More particularly, first, the abnormality change rates in the extracted time-sequential change data are added up. Then, the sum (x) is assessed to determine a total abnormality change. That is to say;

(1) if 2≦x, the total abnormality change is determined as "In progress."

(2) if −1≦x≦1, the total abnormality change is determined as "Unchanged."

(3) if x≦−2, the total abnormality change is determined as "Recovered."

In this embodiment, the sum of the abnormality change rates specified in the time-sequential data of the reference numbers 1, 2, and 3 in Table 25 comes to 11. Therefore, the total abnormality change is determined as "In progress." then compared with the value in "Result of comparing with a previous image" in the interpretation report. The values are "In progress" and agree mutually. Consequently, the finding in the interpretation report is thought to be consistent with the result of CAD processing.

(d) If no abnormality change is extracted from the time-sequential abnormality change data table at the step (b), the operations of the steps (a) to (c) are executed for other findings extracted from the interpretation report by the operation (1).

(e) At this stage, when abnormalities specified in findings extracted by the operation (1) are compared with those in the time-sequential abnormality change data table, if the data values agree mutually, the interpreting doctor's findings on the abnormalities are thought to be consistent with the results of CAD processing. Then, the subsequent steps are not executed.

(f) As for abnormalities specified in findings in an interpretation report and in the time-sequential abnormality change data table whose values disagree mutually, the interpreting doctor's findings on the abnormalities are thought to be inconsistent with the results of CAD processing. Inconsistency may occur in any of the following three cases:

Case 1: an interpreting doctor fails to identify an abnormality change and recognizes normality (no finding), while CAD detects an abnormality change.

Case 2: an interpreting doctor identifies an abnormality change, and CAD also detects an abnormality change but draws a different conclusion |the result of the step (c)|.

Case 3: an interpreting doctor identifies an abnormality change, while CAD fails to detect an abnormality change and recognizes normality.

The control 4a of the workstation WS-1 reads out inconsistent abnormalities from the findings in the interpretation report and the time-sequential abnormality change data table, then stores them separately.

As seen in Table 29 and 25, in this embodiment, reference numbers 4 and 5 in the time-sequential abnormal change data table are specified as inconsistent data.

(g)If data belonging to the aforesaid case 1 or 2 is specified, the control 4a takes the following actions:

1. Outputting a peep sound
2. Displaying a message "CAD points out an abnormality change unfound in the findings." in a terminology display area in the portion of a character display (WSCDISP) 4d for displaying a created interpretation report, if data belonging to the case 1 is found.
3. Displaying a message indicating a finding number and attracting attention; such as, "Finding N: CAD points out a different abnormal change." in the terminology display area in the portion of the character display 4d for displaying a created interpretation report, if data belonging to the case 2 is found. Herein, N represents a finding number in an interpretation report.
4. Retrieving an image (image A) which is acquired in an examination having an examination ID number existent in time- sequential change data indicated with the reference numbers relevant to the case 1 or 2 in the time-sequential abnormality change data table and has an image number existent in the time- sequential abnormality change data, then displaying the image A on the image display (WS-IDISP) 4d.
5. Superimposing overlay data indicating time-sequential abnormality changes relative to the image A on the image A(arrows are colored but not white).
6. Flickering arrows indicating an abnormality change relevant to the case 1 or 2 without flickering other arrows superimposed on the image A. This is the only time when the value of flickering control information in overlay display information is modified to "flickering." Then, the modified data is transmitted to an image display manager 4h.
7. Retrieving an image (image B) which is acquired in an examination having an examination ID number of a previous examination existent in time-sequential change data indicated with the reference numbers relevant to the case 1 or 2 in the time-sequential abnormality change data table and has an image number existent in the time-sequential abnormality change data, then displaying the image B on the image display 4d. The image B is displayed by the image A.
8. Superimposing overlay data indicating the results of detecting abnormalities in the image B on the image B (white arrow).

FIG. 23 shows an interpretation report creation screen of a character display (WS-CDISP) 4d at this stage in this embodiment. 61 denotes a CRT screen of the character display 4d.

Figure 24A:
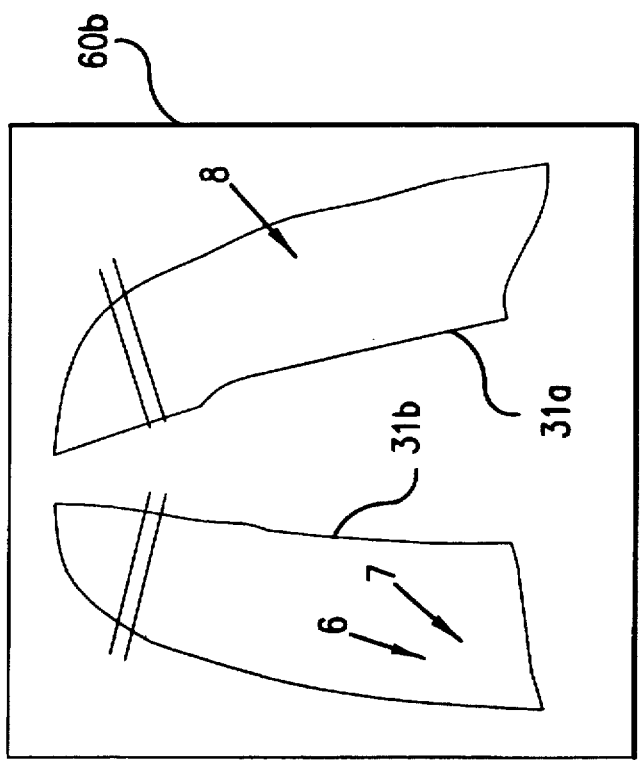
FIG. 24 shows a screen of the image display of a workstation on which overlay data is superimposed on an image.
Figure 24B:
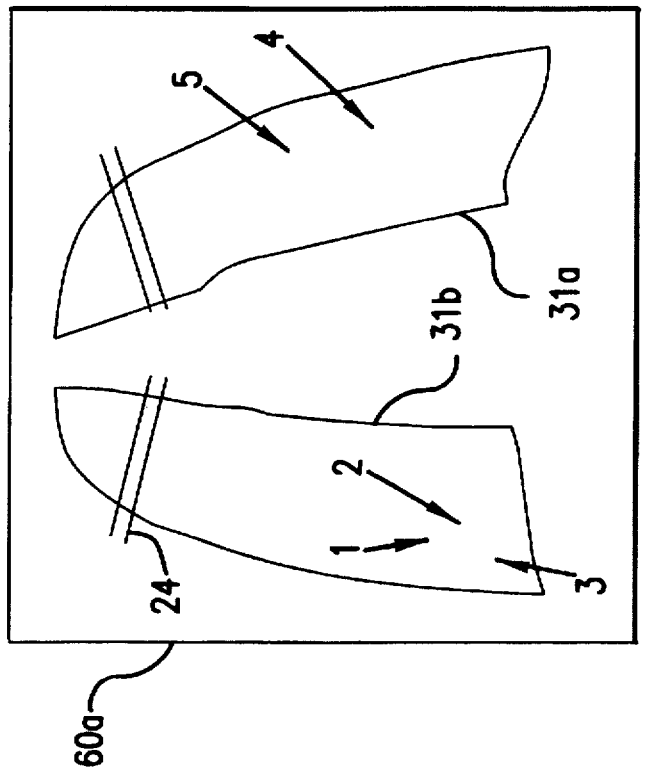

FIG. 24 shows an image and overlay data displayed on an image display (WS-IDISP) 4i. In FIG. 24, 60a and 60b denote the CRT screens of the first and second image displays on the left among four image displays 4i lined sideways as shown in FIG. 18. In FIG. 24, the CRT screen 60a displays an image specified with an examination ID number 103541 and an image number 1, and the CRT 60b, an image specified with an examination ID number 100902 and an image number 1. 30a, 30b, and 24 represent the left lung field, right lung field, and clavicle.

In FIG. 24, ① to ⑧ are assigned to arrows (arrows ① to ⑤ are on the CRT screen 60a, and arrows ⑥ to ⑧, on the CRT screen 60b) for easy recognition of positions of abnormalities. These encircled numbers correspond to the reference numbers in Table 24. An arrow ① indicates coordinates (350, 1350) in yellow, an arrow ②, coordinates (400, 1500) in yellow, and an arrow ③, coordinates (350, 1600) in red. An arrow ④ indicates coordinates (1600, 1300) in red and flickers. An arrow ⑤ indicates coordinates (1500, 800) in blue and flickers. An arrow ⑥ indicates coordinates (350, 1350) in white, an arrow ⑦, coordinates (400, 1500) in white, and an arrow ⑧, coordinates (1500, 800) in white. Thus, the image on the CRT screen 60a on which the arrows ① to ⑤ are overlaid provides time-sequential abnormality change information.

An interpreting doctor's attention is not called in the case 3. This is because the current CAD technology creates areas in an image in which no abnormality can be detected. An interpreting doctor may identify an abnormality change in any of the areas. With the advancement of the technology, such areas in which no abnormality can be detected will become inexistent. Then, an interpreting doctor's attention will be called in the case 3. Specifically, a message indicating a finding number and attracting attention; such as, "Finding 1: CAD points out no abnormality change but recognizes normality." may be displayed in a terminology display area in the portion of a character display (WS-CDISP) 4d for displaying a created interpretation report. 7. Referencing the Results of CAD Processing by an Interpreting Doctor An interpreting doctor references a displayed image and arrows. If necessary, the doctor can display the results of CAD processing; that is, an abnormality data table and a time-sequential abnormality change data table on a character display (WS-CDISP) 4d. For this display, the doctor enters a command, examination ID number, and image number at an input unit (WS-INPUT) 4c.

Overlay data can be superimposed on a designated image. For the superimposition, the interpreting doctor enters a command, examination ID number, and image number at the input unit 4c.

(1) When an interpreting doctor attempts to superimpose overlay data on an image, a workstation acts as described below.

(a) An interpreting doctor enters a command, examination ID number, and image number at an input unit 4c.

(b) A control (WS-CRTL) 4a of a workstation determines whether a designated image is an image to which CAD can apply. The procedure of determination is identical to that described in subsection 4.1.1) of (1) CAD processing of section 4 "Executing CAD Processing and Creating Diagnostic Information."

(c) If an applicable abnormality detection means is unavailable, the control 4a displays "An abnormality detection means applicable to the designated image is unavailable." on a character display (WS-CDISP) 4d. Thereby, the interpreting doctor learns that CAD does not apply to the designated image.

(d) If an applicable abnormality detection means is available, the control 4a references the abnormality data table to see if any abnormality is detected in the image.

(e) If an abnormality is detected, overlay display information associated with the designated image, and other information required for superimposing overlay data on the image are sent to an image display manager 4h. Then, the overlay data is superimposed on the image on an image display (WS-IDISP) 4i.

(f) If no abnormality is detected, overlay data associated with the image does not reside. The control 4a displays the designated image on the image display 4i and "No abnormality is detected in the designated image." on the character display 4d.

Thereby, the interpreting doctor learns that CAD processing detects no abnormality in the designated image. At present, however, this does not mean that the image shows normality. This is because the current CAD technology restricts areas in which abnormalities can be detected and limits types of detectable abnormalities. Therefore, the interpreting doctor must be aware of the underlying meanings of the message.

(2) When an interpreting doctor attempts to display a time-sequential abnormality change data table and other diagnostic information resulting from CAD processing, a workstation acts based on the aforesaid concept. That is to say;

(a) if a designated image is not an image to which CAD can apply, the fact is indicated on a character display (WS-CDISP) 4d.

(b) If no abnormality is detected in the designated image, the fact is indicated in the character display 4d.

This information may appear automatically within the system operation described in section 6 "Comparing Diagnostic Information and Calling Interpreting Doctor's Attention."

8. Completing and Storing an Interpretation Report (1) Completing an interpretation report (a) An interpreting doctor uses an input unit (WS-INPUT) 4d to modify an interpretation report which has been entered immediately before, if necessary. A control (WS-CTRL) 4a of a workstation WS-1 modifies the interpretation report stored in system memory, then displays the modified data in an interpretation report creation area in a character display (WS-CDISP) 4d.

(b) After completing modification, the interpreting doctor enters an interpretation termination command at the input unit 4d.

(c) The control 4a displays a prompt for input of an interpreting doctor ID number on the character display. The interpreting doctor enters his/her interpreting doctor ID number. The control 4a checks if the entered interpreting doctor ID number resides in the interpreting doctor information table (Table 14). If the ID number resides, the control 4a retrieves an interpreting doctor name corresponding to the interpreting doctor ID number as an interpreting doctor name and appends the name to the interpretation report.

(d) The control 4a appends the values of the data items from "Patient ID number" to "Date of interpretation" included in the interpretation report of Table 7, to the findings and conclusion in the created interpretation report. The data values except an interpreting doctor name and a date of interpretation are included in the patient examination history.

The value determined at a step (c) is specified as the interpreting doctor name.

A built-in clock of the workstation is used to determine the date of interpretation.

(2) Transferring and storing an interpretation report (a) A control (WS-CTRL) 4a of a workstation WS-1 sends a completed interpretation report to a network interface (WS-NWIF), then instructs the network interface to transfer the interpretation report to a system manager (SM) 1. The network interface 4j sends the interpretation report to the system manager 1.

(b) When the interpretation report sent from the workstation reaches the network interface 4j of the system manager 1, a control (SM-CTRL) 4a of the system manager 1 reads the interpretation report from a network interface (SM-NWIF) 1h, then writes the data in system memory of the control 4a. The control 4a transfers the interpretation report from the system memory to an interpretation report storage (SM-IDRM) if for storage.

Thus, a sequence of jobs starting with receiving examination request information and ending with completing and storing an interpretation report is complete.

The present invention is not restricted to the system of the aforesaid embodiment. Variants will be described below.

In item (3) "Creating a time-sequential abnormality change data table" in section 4 describing a system operation "Executing CAD Processing and Creating Diagnostic Information," abnormalities whose types and positions agree are compared mutually at a step (b) in subsection 4.3.1). However, positions of abnormalities do not always agree perfectly. As far as a deviation between positions of abnormalities is within a certain distance, the positions may be recognized as the same. This will realize more practical comparison.

More particularly, in this embodiment, when a lung field area containing an abnormality is determined according to item (2) "Determining lung field area containing an abnormality" in section 4 "Executing CAD Processing and Creating Diagnostic Information," the same area is specified in images compared. A position of an abnormality is also the same between images compared.

However, positions in images seldom coincide when the images are acquired on different dates of examination. Therefore, it is recommended to (1) align images in advance or (2) detect a positional deviation and correct the positional data in an abnormality data table.

In the aforesaid embodiment, when a CAD processor (WS-CADP) 4e determines an area in an image (for example, the left superior lung field or left central lung field), the CAD processor 4e flattens the coordinates of the right and left infraclavicular margins and those of the right and left supradiaphragmatic margines, then uses the flattened values to determine the borders among the superior, central, and inferior lung fields. However, the borders among the superior, central, and inferior lung fields may be calculated independently for each of the right and left lung fields.

In the aforesaid embodiment, two image consisting of an interpretation image and a previous image are used to create a time-sequential abnormality change data table. Two or more images can also be compared.

In the aforesaid embodiment, time-sequential abnormality changes are indicated by overlaying arrows of different colors. Positions of abnormalities may be enclosed with various graphics. Then, time-sequential changes may be differentiated with the graphics (○, ◊, □, △.).

In the aforesaid embodiment, three kinds of abnormality detection means (for detecting pulmonary interstitial disease, pulmonary nodules, and fine calcification) are incorporated. Any kind of abnormality detection means may be incorporated, and any type of images (CT or MRI images except X-ray images) may be handled.

The result of comparing data in an abnormality data table or time-sequential abnormality change data table with each finding in an interpretation report is displayed on a character display 4d, which may, however, be provided as a voice output using a speech synthesis technology. Operators and doctors may be able to enter data with voice at an input unit (FDG-INPUT) 2d of a film digitizer 2 or an input unit (WS-INPUT) 4c of a workstation.

In the embodiment, images are evaluated. Examination data except images; such as, graphic data including electrocardiographs and electroencephalograms or numerical values an automated chemical analysis apparatus provides may be dealt with.

In the aforesaid embodiment, a CAD processor (WS-CADP) compares multiple plain X-ray images acquired in the same patient's same region on different dates of examination. However, if a corresponding knowledge database is available, images of different regions, images of different types (for example, X-ray and MRI images), or examination data of different types (medical images and electrocardiographs) may be compared for CAD.

In the embodiment, a doctor's interpretation report is compared with the results of CAD processing. However, for mass screening, multiple doctors' interpretation reports may be compared with one another. Furthermore, the results of applying CAD processing to time-sequential changes detected in images of the same type may be compared with the results of applying CAD processing to images of different types. That is to say, results of CAD processing can be compared mutually.

In the embodiment, a control (WS-CTRL) 4a of a workstation is used to compare a doctor's interpretation report with the results of CAD processing and obtain the resultant. The control 4a may be replaced with a CPU in a unit which is designed exclusively for comparing multiple diagnostic information and providing the resultant, and connected on a network 5. When data (results of CAD processing or results of a doctor's diagnosis) existent in a database 3 is compared to provide the resultant, a control (DB-CTRL) 3a of the database 3 may be used.

In the aforesaid embodiment, the relational information defining a relation between the image display and the imaging direction or the modality is stored in the workstation 4 in the light of additional information.

However, the relational information may be stored in the database or the data acquisition apparatus.

In this case,the workstation requests the database or the data acqusition apparatus to send the relational information to the workstation and then display the image according to the relational information.

The relational information defining an imaging direction and modality of each image may be made by each doctor.

In this case,the workstation can receive an ID number of each doctor,and can select a relational information corresponding to the doctor as part of an additional information.

In the aforesaid embodiment,the information inputting means and the information deciding means are provided in the data acqusition apparatus,but may be provided in the workstation,or the database.

In the aforesaid embodiment,the display position determining means is provided in the control of the workstation of the PACS,but may be provided in the workstation of PACS independently.

In addition,the display position determining means can be used in a stand-alone display system,for example,a display system comprising a data acqusition apparatus and a workstation,or comprising a workstation only.

What is claimed is:

1. A medical information processing system for supporting diagnostic interpretation, which has a workstation having a storage unit for storing data, the system comprising:

data storage means having a memory means for storing examination data of an object to be examined including interpretation data to be interpreted and interpretation reference data to be referenced during interpretation of the interpretation data, said data storage means being apart from the workstation;

data loading means comprising:

specifying means for specifying a priority order in loading of the interpretation reference data in conjunction with the given interpretation data; and instructing means for instructing a workstation control means and a memory control means to load the interpretation data and the interpretation reference data from the memory means of the data storage means into the storage unit of the workstation, the interpretation reference data being loaded according to the priority order specified by the specifying means;

diagnostic information creating means for creating diagnostic information relative to the examination data loaded in the storage unit of the workstation;

diagnostic information comparing means for comparing a plurality of the diagnostic information with each other; and diagnostic information output means for outputting at least one of the created diagnostic information and information concerning results compared by the diagnostic information comparing means.

2. A medical information processing system according to claim 1, wherein said diagnostic information creating means comprises:

creating means for creating diagnostic information of findings relative to at least one of the interpretation data and the interpretation reference data; and input means for inputting the created diagnostic information into the medical information processing system.

3. A medical information processing system according to claim 1 wherein said diagnostic information creating means comprises computerizing means for creating diagnostic information relative to at least one of said interpretation data and said interpretation reference data.

4. A medical information processing system according to claim 3 wherein said computerizing means comprises:

abnormality detection means capable of detecting lesion;

applying means for applying said abnormality detection means to predetermined examination data; and acquiring means for acquiring diagnostic information.

5. A medical information processing system according to claim 4 wherein said computerizing means further comprises:

memory means for storing abnormality detection means select information for associating said abnormality detection means with items of examination data to which the abnormality detection means can be applied.

6. A medical information processing system according to claim 4 wherein said computerizing means further comprises creation means for creating diagnostic information indicating the positions of abnormalities in which said lesions are detected and the degrees of the abnormalities.

7. A medical information processing system according to claim 6 wherein said computerizing means further comprises:

calculating means for calculating said positions of abnormalities in association with image areas of at least one of said interpretation data and said interpretation reference data; and output means for outputting the calculated positions of abnormalities as locations in an image in which said diagnostic information is displayed.

8. A medical information processing system according to claim 3, wherein said diagnostic information comparing means has a mechanism for calculating differences between the diagnostic information as time-sequential abnormality change data.

9. A medical information processing system according to claim 8 wherein said time-sequential abnormality change data includes predetermined indices representing the progresses of the abnormalities of interest.

10. A medical information processing system according to claim 8 wherein said diagnostic information output means comprises superimposing means for superimposing the contents of said time-sequential abnormality change data on associated examination data in a mutually-discernible manner.

11. A medical information processing system according to claim 1 wherein said diagnostic information creating means comprises computerizing means for creating diagnostic information relative to at least one of said interpretation data and said interpretation reference data and said diagnostic information comparing means comprises comparing means for comparing first diagnostic information created as findings with second diagnostic information which said computerizing means creates.

12. A medical information processing system according to claim 11 wherein said first diagnostic information is an interpretation report and said second diagnostic information is abnormality data.

13. A medical information processing system according to claim 11 wherein said first diagnostic information is an interpretation report and said second diagnostic information is time-sequential abnormality change data.

14. A medical information processing system according to claim 11 wherein said diagnostic information output means outputs a message for an inconsistency of said first diagnostic information with said second diagnostic information.

15. A medical information processing system according to claim 14 wherein said message includes at least one of a signal sound, synthetic voice, characters and images.

16. A medical information processing system according to claim 14 wherein said diagnostic information output means comprises superimposing means for superimposing said second diagnostic information on corresponding examination data in such a display format that an abnormality positions of said second diagnositic information and said inconsisitency can be identified clearly.

17. A medical information processing system according claim 1, wherein all of said diagnostic information creating means, diagnostic information comparing means and diagnostic information output means are composed of components of the workstation.

18. A medical information processing system according to claim 17, wherein said specifying means comprises:

memory means for storing interpretation reference data loading rule information being changeable by rewriting;

creating means for creating interpretation reference priority information based on the interpretation reference data loading rule information; and determining means for determining the priority order according to the created interpretation reference priority information.

19. A medical information processing system according to claim 18, wherein said interpretation reference data loading rule information includes at least information in terms of an examined region, a same examined region being given to a first priority.

20. A medical information processing system according to claim 19, wherein said interpretation reference data loading rule information includes further information in terms of a modality and a date of examination, a same modality being given to a second priority and a latest date of examination being given to a third priority.

21. A medical information processing system according to claim 20, wherein said data loading means further comprises sending means for sending information including at least the interpretation reference priority information into the storage unit of the workstation.

22. A medical information processing system according to claim 21, wherein said sending means further sends at least one of an examination request information, examination histories, and interpretation reports.

23. A medical information processing system according to claim 18, wherein said workstation is composed of a plurality of workstations operatively connected with each other and said data loading means further comprises memory means for storing workstation vs. interpretation examination modality information which associates the interpretation data with the plurality of workstations, workstation determining means for determining one of the plurality of workstations into which the interpretation data is loaded, according to the workstation vs. interpretation examination modality information, and workstation selecting means for selecting the one workstation determined by the workstation determining means.

24. A medical information processing system according to claim 18, wherein said memory means of the data storage means comprises a low-speed memory medium and a high-speed memory medium for storing the examination data therein.

25. A medical information processing system according to claim 24, wherein said instructing means comprises memory control means for controlling input and output of the examination data to and from the memory means of the data storage means, the memory control means having a data transferring mechanism for transferring the interpretation reference data from the low-speed memory medium to the high-speed memory medium on the basis of the priority order.

26. A medical information processing system according to claim 18, wherein said instructing means comprises workstation control means for controlling input and output of the data to and from the storage unit of the workstation, the workstation control means having a request mechanism for requesting the data storage means to send the interpretation reference data to the workstation according to the priority order.

27. A medical information processing system according to claim 1, wherein said workstation comprises a plurality of displays for displaying a plurality of medical examination images and display position determining means for automatically determining an assignment of each of the plurality of medical examination images to the plurality of displays based on information defining at least a relation between imaging directions of the plurality of medical examination images and relative image display positions among the plurality of medical examination images.

28. A medical information processing system according to claim 1, wherein said workstation is a workstation of a picture archiving and communication system having a database and system manager to both of which the workstation is operatively connected.

29. A medical information processing system according to claim 28, wherein said data storage means is composed of a memory member of the database of the picture archiving and communication system and said data loading means is formed by mutually combining the system manager, a control member of the database and a control member of the workstation of the picture archiving and communication system.

30. A medical information processing system for supporting diagnostic interpretation, which has a workstation having a storage unit for storing data, the system comprising:
    data storage means having a memory means for storing examination data of an examined object, the examination data including interpretation data to be interpreted and interpretation reference data to be referenced during interpretation of the interpretation data; and
    a data loading means comprising:
        specifying means for specifying, on the basis of interpretation reference data loading rule information, a priority order in loading of the interpretation reference data in conjunction with the interpretation data which has been given; and
        an instructing means for instructing loading of the given interpretation data and the interpretation reference data from the memory means of the data storage means into the storage unit of the workstation, the interpretation reference data being loaded according to the priority order specified by the specifying means;
        wherein said interpretation reference data loading rule information includes information representing a region of the object, a modality, and a date related to examination of the object.

31. A medical information processing system according to claim 30, wherein said data loading means further comprises a sending means for sending information including at least the interpretation reference priority information into the storage unit of the workstation.

32. A medical information processing system according to claim 31, wherein said sending means further sends at least one of an examination request information, examination histories, and interpretation reports.

33. A medical information processing system according to claim 32, wherein said workstation, data storage means, and data loading means are connected with each other through a network.

34. A medical information processing system according to claim 33, wherein said network is connected with an examination order system from which the examination request information is provided.

35. A medical information processing system according to claim 30, wherein said workstation is composed of a plurality of workstations operatively connected with each other and said data loading means further comprises memory means for storing workstation vs. interpretation examination modality information which associates the interpretation data with the Plurality of workstations, workstation determining means for determining one of the plurality of workstations into which the interpretation data is loaded, according to the workstation vs. interpretation examination modality information, and workstation selecting means for selecting the one workstation determined by the workstation determining means.

36. A medical information processing system according to claim 30, wherein said modality includes at least one of an ultrasonic diagnostic apparatus, X-ray diagnostic apparatus, X-ray computed tomography system and magnetic resonance imaging system.

37. A medical information processing system according to claim 36, wherein said modality is connected with the data storage means through a network.

38. A medical information processing system according to claim 30, wherein said memory means of the data storage means comprises a low-speed memory medium and a high-speed memory medium for storing the examination data therein.

39. A medical information processing system according to claim 38, wherein said low-speed memory medium is an optical disk and said high-speed memory medium is a magnetic disk.

40. A medical information processing system according to claim 39, wherein said instructing means comprises memory control means for controlling input and output of the examination data to and from the memory means of the data storage means, the memory control means having a data transferring mechanism for transferring the interpretation reference data from the low-speed memory medium to the high-speed memory medium on the basis of the priority order.

41. A medical information processing system according to claim 30, wherein said instructing means comprises workstation control means for controlling input and output of the data to and from the storage unit of the workstation, the workstation control means having a request mechanism for requesting the data storage means to send the interpretation reference data to the workstation according to the priority order.

42. A medical information processing system according to claim 30, wherein said data storage means is composed of a memory member of a data base of a picture archiving and communication system and said data loading means comprises a system manager, a control member of the database and a control member of the workstation of the picture archiving and communication system.

43. A medical information processing system according to claim 42, wherein said data loading means further comprises sending means for sending information including at least the interpretation reference priority information into the storage unit of the workstation.

44. A medical information processing system according to claim 43, wherein said sending means further sends at least one of an examination request information, examination histories, and interpretation reports.

45. A medical information processing system according to claim 44, wherein said workstation comprises an image display for displaying at least one of the interpretation data, interpretation reference data, examination request information, examination histories, interpretation reference priority information and interpretation reports.

46. A medical information processing system according to claim 42, wherein said workstation is composed of a plurality of workstations operatively connected with each other and said data loading means further comprises memory means for storing workstation vs. interpretation examination modality information which associates the interpretation data with the plurality of workstations, workstation determining means for determining one of the plurality of workstations into which the interpretation data is loaded, according to the workstation vs. interpretation examination modality information, and workstation selecting means for selecting the one workstation determined by the workstation determining means.

47. A medical information processing system according to claim 42, wherein said memory means of the data storage means comprises a low-speed memory medium and a high-speed memory medium for storing the examination data therein.

48. A medical information processing system according to claim 47, wherein said instructing means comprises memory control means for controlling input and output of the examination data to and from the memory means of the data storage means, the memory control means having a data transferring mechanism for transferring the interpretation reference data from the low-speed memory medium to the high-speed memory medium based on the priority order.

49. A medical information processing system according to claim 42, wherein said instructing means comprises workstation control means for controlling input and output of the data to and from the storage unit of the workstation, the workstation control means having a request mechanism for requesting the data storage means to send the interpretation reference data to the workstation according to the priority order.

50. A medical information processing system according to claim 42, wherein said interpretation reference data loading rule information includes further information in terms of a modality and a date of examination, a same modality being given to a second priority and a latest date of examination being given to a third priority.

51. A medical information processing system according to claim 30, wherein information representing said region is given to a first priority, information representing said modality is given to a second priority, and information representing said date is given to a third priority.

52. A medical information processing system according to claim 30, wherein said region is substantially the same region as an examined region of the object.

53. A medical information processing system according to claim 30, wherein said specifying means comprises:

memory means for storing in advance the interpretation reference data loading rule information changeable by rewriting stored data of the memory means;

creating means for creating interpretation reference priority information based on the interpretation reference data loading rule information; and determining means for determining the priority order according to the created interpretation reference priority information.

54. A medical information processing system according to claim 30, wherein said modality is a same kind of modality as a modality acquiring the interpretation data.

55. A medical information processing system according to claim 30, wherein said date is a latest examination date of the object, latest data among the interpretation reference data having been acquired on said latest date.

* * * * *